US00RE40722E

(19) United States
(12) Reissued Patent
Chappa

(10) Patent Number: US RE40,722 E
(45) Date of Reissued Patent: Jun. 9, 2009

(54) METHOD AND APPARATUS FOR COATING OF SUBSTRATES

(75) Inventor: Ralph A. Chappa, Prior Lake, MN (US)

(73) Assignee: SurModics, Inc., Eden Prairie, MN (US)

(21) Appl. No.: 11/823,055

(22) Filed: Jun. 26, 2007

Related U.S. Patent Documents

Reissue of:
(64) Patent No.: 7,125,577
Issued: Oct. 24, 2006
Appl. No.: 10/976,348
Filed: Oct. 27, 2004

U.S. Applications:
(63) Continuation-in-part of application No. 10/256,349, filed on Sep. 27, 2002, now Pat. No. 7,192,484.

(51) Int. Cl.
*A61L 33/00* (2006.01)
*B05D 1/02* (2006.01)

(52) U.S. Cl. ..... 427/2.24; 427/2.1; 427/421.1; 427/425; 118/300; 118/320; 118/311

(58) Field of Classification Search ..... 427/2.24, 427/2.1, 421.1; 118/300, 320, 311
See application file for complete search history.

(56) References Cited

U.S. PATENT DOCUMENTS

| | | | | |
|---|---|---|---|---|
| 1,866,100 | A | | 7/1932 | Hach |
| 2,253,019 | A | | 8/1941 | Crepeau |
| 2,330,880 | A | | 10/1943 | Gladfelter et al. |
| 2,493,787 | A | | 1/1950 | Torretti |
| 3,198,170 | A | | 8/1965 | Toshio |
| 3,318,281 | A | * | 5/1967 | Plegat ..... 118/672 |
| 3,935,896 | A | | 2/1976 | Tegtmeier et al. |
| 3,963,069 | A | | 6/1976 | Marti et al. |
| 4,051,805 | A | | 10/1977 | Waldrum |
| 4,060,116 | A | | 11/1977 | Frailly |
| 4,073,335 | A | | 2/1978 | Fort et al. |
| 4,075,975 | A | | 2/1978 | Oswald |
| 4,153,201 | A | | 5/1979 | Berger et al. |
| 4,174,678 | A | | 11/1979 | Van Den Bergh |

(Continued)

FOREIGN PATENT DOCUMENTS

| | | | |
|---|---|---|---|
| CA | 2351016 | | 12/2001 |
| DE | 33 35 502 | C1 | 3/1985 |
| DE | 33 35 502 | | 3/1985 |
| WO | WO-00/01322 | | 1/2000 |
| WO | WO-01/32382 | A1 | 5/2001 |
| WO | WO-01/32382 | | 5/2001 |
| WO | WO-02/20174 | | 3/2002 |
| WO | WO-02/20174 | A1 | 3/2002 |
| WO | WO-03/004072 | | 1/2003 |
| WO | WO-03/004072 | A2 | 1/2003 |
| WO | WO-2004/028579 | | 4/2004 |
| WO | WO-2004/028699 | | 4/2004 |
| WO | WO-2004/037443 | | 5/2004 |
| WO | WO-2004/037443 | A1 | 5/2004 |

*Primary Examiner*—William Phillip Fletcher, III
*Assistant Examiner*—Cachet I Sellman
(74) *Attorney, Agent, or Firm*—Pauly, DeVries Smith & Deffner, L.L.C.

(57) ABSTRACT

The invention relates to methods and apparatuses that reduce problems encountered during coating of a device, such as a medical device having a cylindrical shape. In an embodiment, the invention includes an apparatus including a bi-directional rotation member. In an embodiment, the invention includes a method with a bi-directional indexing movement. In an embodiment, the invention includes a coating solution supply member having a major axis oriented parallel to a gap between rollers on a coating apparatus. In an embodiment, the invention includes a device retaining member. In an embodiment, the invention includes an air nozzle or an air knife. In an embodiment, the invention includes a method including removing a static charge from a small diameter medical device.

12 Claims, 25 Drawing Sheets

U.S. PATENT DOCUMENTS 4,240,373 A * 12/1980 Anger ..... 118/301
4,289,089 A 9/1981 Tacke et al.
4,301,968 A 11/1981 Berger et al.
4,337,896 A 7/1982 Berger et al.
4,352,459 A 10/1982 Berger et al.
4,375,820 A 3/1983 Vinarcsik et al.
4,541,564 A 9/1985 Berger et al.
4,567,934 A 2/1986 Nakao et al.
4,572,451 A 2/1986 Ikeda et al.
4,638,045 A 1/1987 Kohn et al.
4,655,393 A 4/1987 Berger
4,723,708 A 2/1988 Berger et al.
4,978,067 A 12/1990 Berger et al.
5,183,509 A 2/1993 Brown et al.
5,219,120 A 6/1993 Ehrenberg et al.
5,387,247 A 2/1995 Vallana et al.
5,413,638 A 5/1995 Bernstein, Jr. et al.
5,501,735 A 3/1996 Pender
5,527,389 A 6/1996 Rosenblum et al.
5,643,362 A 7/1997 Garves
5,656,332 A 8/1997 Saito et al.
5,658,387 A 8/1997 Reardon et al.
5,833,891 A 11/1998 Subramaniam et al.
5,837,088 A 11/1998 Palmgren et al.
5,882,405 A 3/1999 Kish et al.
5,897,911 A 4/1999 Loeffler
6,153,252 A 11/2000 Hossainy et al.
6,156,373 A 12/2000 Zhong et al.
6,203,551 B1 3/2001 Wu
6,254,921 B1 7/2001 Chappa et al.
6,322,847 B1 11/2001 Zhong et al.
6,333,595 B1 12/2001 Horikawa et al.
6,345,630 B2 2/2002 Fishkin et al.
6,358,556 B1 3/2002 Ding et al.
6,368,658 B1 4/2002 Schwarz et al.
6,395,326 B1 5/2002 Castro et al.
6,406,754 B2 6/2002 Chappa et al.
6,431,770 B1 8/2002 Kurematsu et al.
6,506,437 B1 1/2003 Harish et al.
6,517,889 B1 2/2003 Jayaraman
6,521,299 B1 * 2/2003 Dessauer ..... 427/471
6,527,863 B1 3/2003 Pacetti et al.
6,544,582 B1 4/2003 Yoe
6,555,157 B1 4/2003 Hossainy
6,562,136 B1 * 5/2003 Chappa et al. ..... 118/500
6,565,659 B1 5/2003 Pacetti et al.
6,572,644 B1 6/2003 Moein
6,605,154 B1 8/2003 Villareal
6,607,598 B2 8/2003 Schwarz et al.
6,616,765 B1 9/2003 Wu et al.
6,669,980 B2 12/2003 Hansen
6,673,154 B1 1/2004 Pacetti et al.
6,676,987 B2 1/2004 Zhong et al.
6,695,920 B1 2/2004 Pacetti et al.
6,709,514 B1 3/2004 Hossainy
6,709,712 B2 3/2004 Chappa et al.
6,725,901 B1 4/2004 Kramer et al.
6,743,462 B1 6/2004 Pacetti
6,743,463 B2 6/2004 Weber et al.
6,783,793 B1 8/2004 Hossainy et al.
6,803,070 B2 10/2004 Weber
7,125,577 B2 10/2006 Chappa
7,192,484 B2 3/2007 Chappa et al.
2001/0001824 A1 5/2001 Wu
2002/0051730 A1 5/2002 Bodnar et al.
2002/0094440 A1 7/2002 Llanos et al.
2002/0103526 A1 8/2002 Steinke
2002/0115400 A1 8/2002 Skrmetta
2002/0155212 A1 10/2002 Hossainy
2003/0003221 A1 1/2003 Zhong et al.
2003/0044514 A1 3/2003 Richard
2003/0054090 A1 3/2003 Hansen
2003/0059520 A1 3/2003 Chen et al.
2003/0088307 A1 5/2003 Shulze et al.
2003/0113439 A1 6/2003 Pacetti et al.
2003/0150380 A1 8/2003 Yoe
2003/0157241 A1 8/2003 Hossainy et al.
2004/0062875 A1 4/2004 Chappa et al.
2004/0073298 A1 4/2004 Hossainy
2004/0081745 A1 4/2004 Hansen
2004/0161547 A1 8/2004 Carlson et al.
2004/0185168 A1 9/2004 Weber et al.
2005/0098097 A1 5/2005 Chen et al.
2006/0096535 A1 5/2006 Haller et sl.

* cited by examiner

FIG. 1
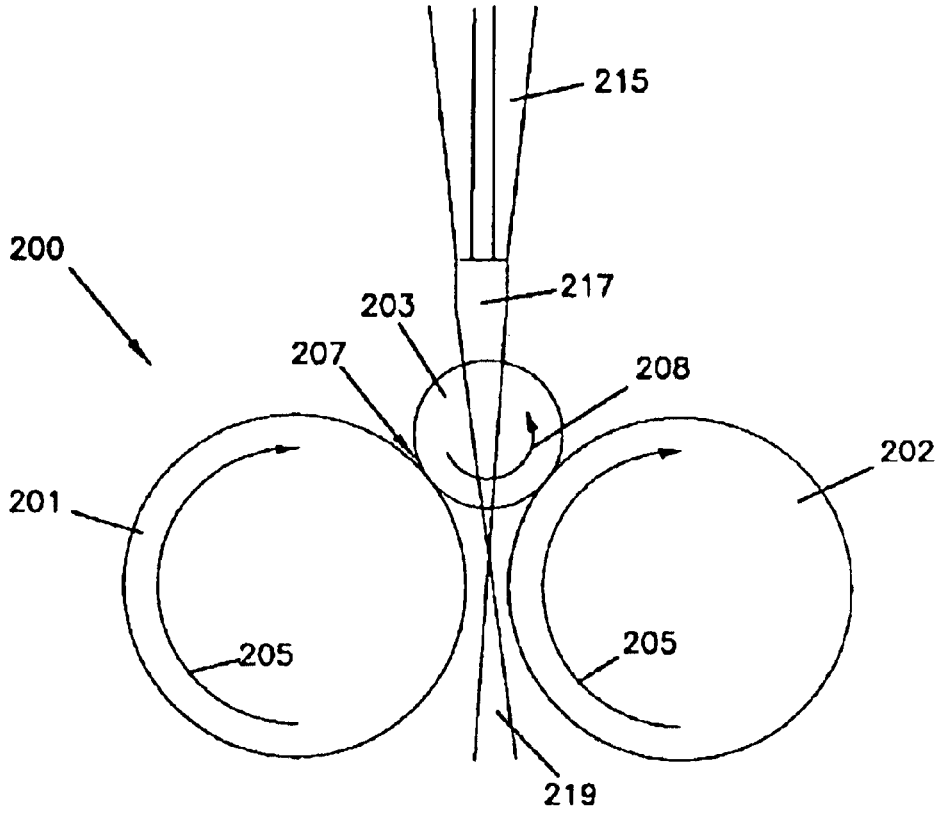
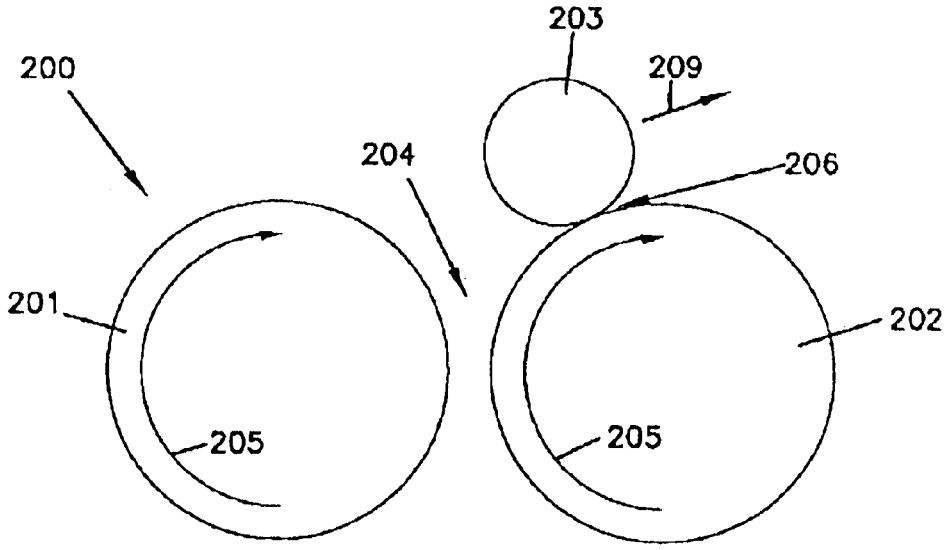
FIG. 2

FIG. 19
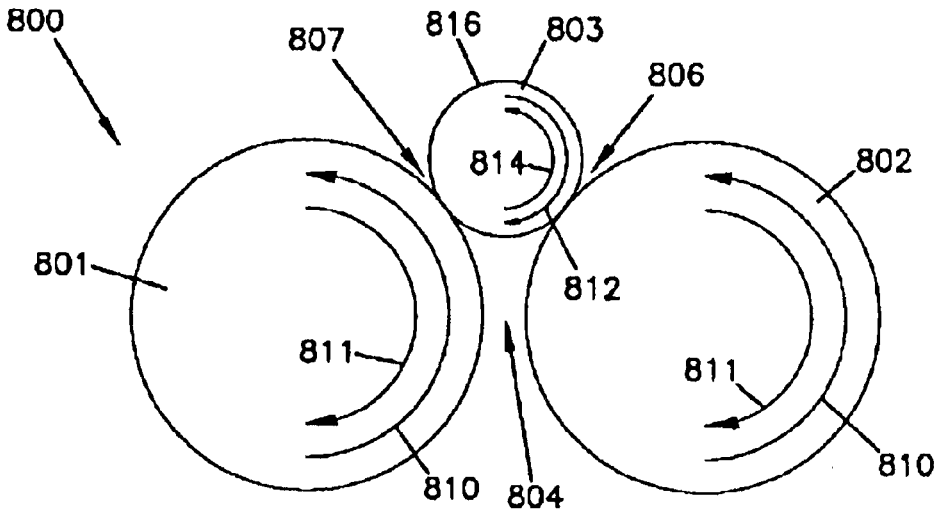
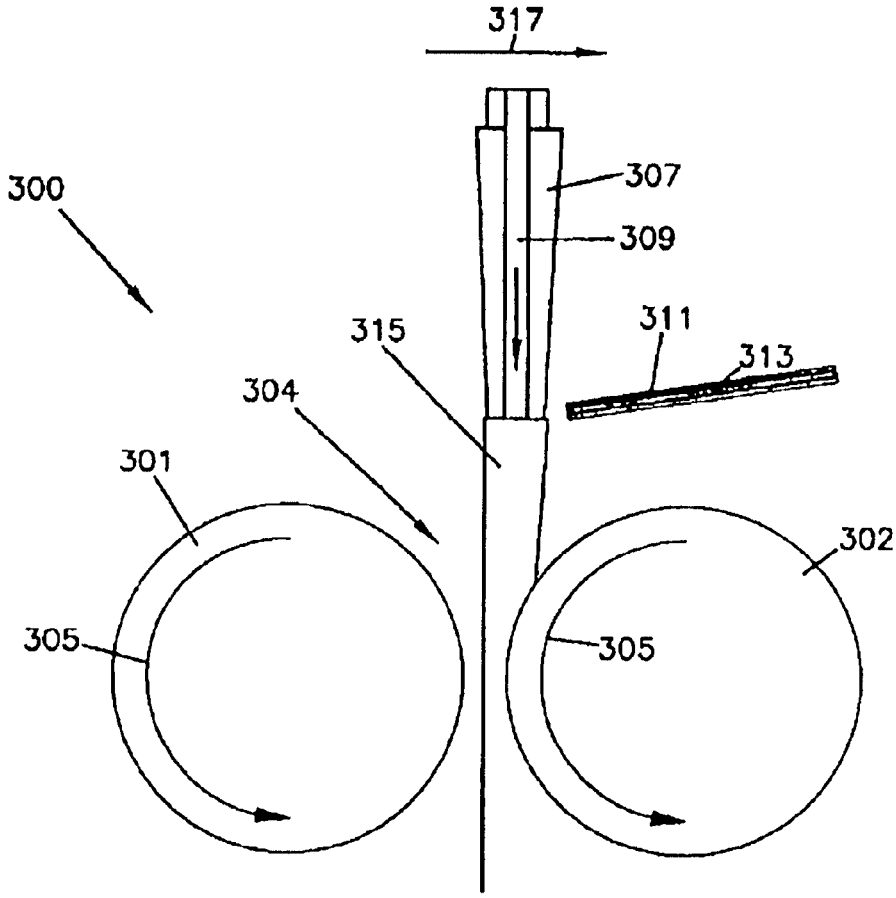
FIG. 20

FIG. 21
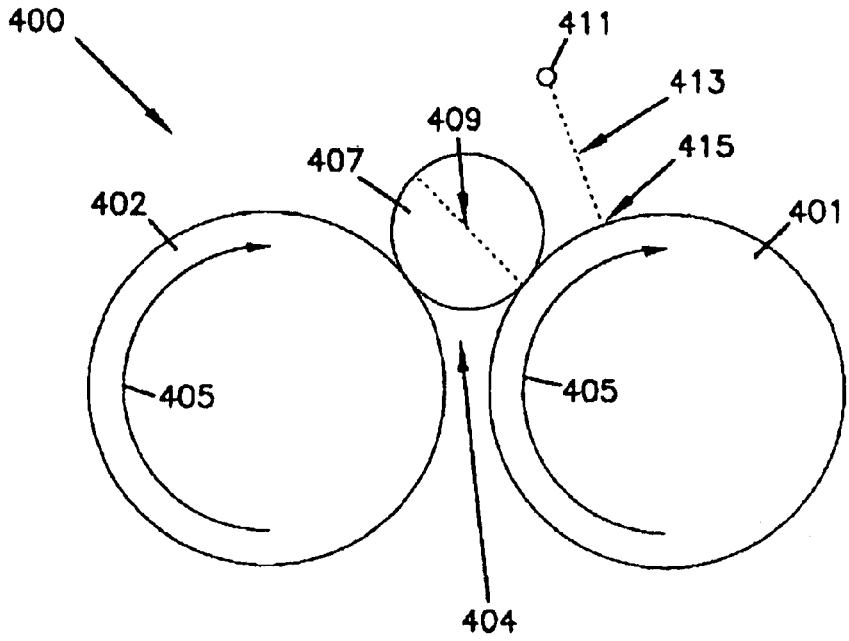
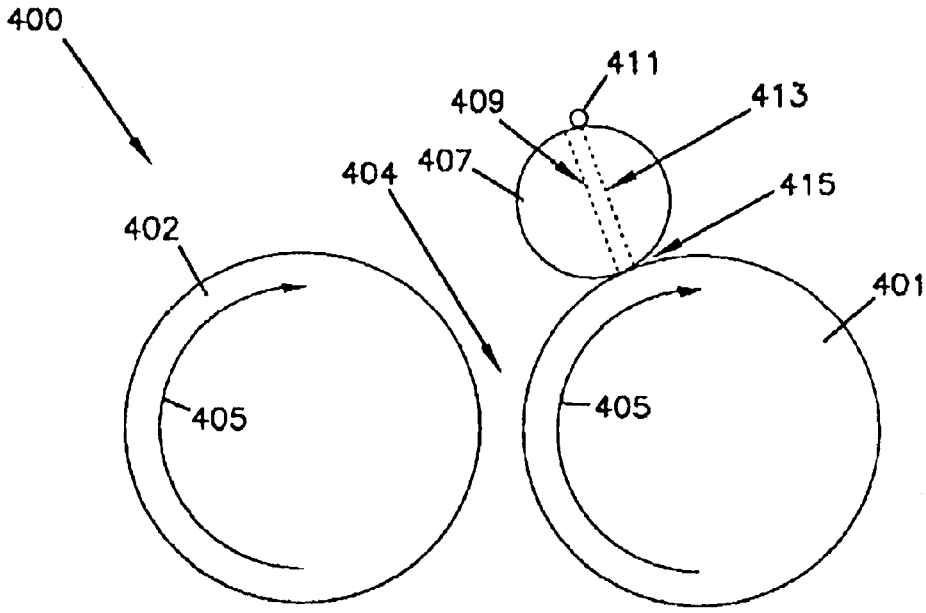
FIG. 22

FIG. 26
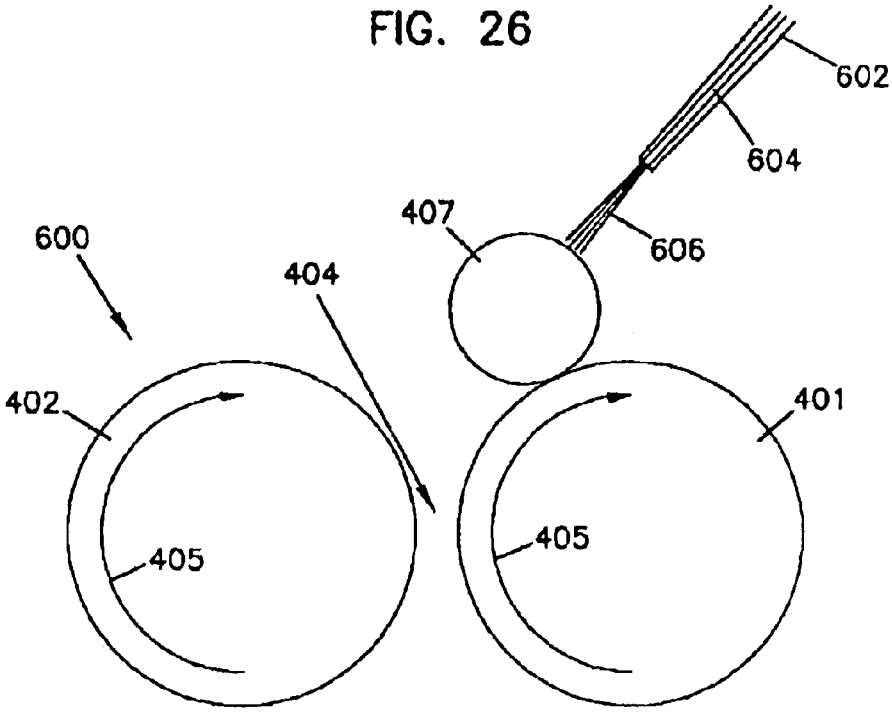
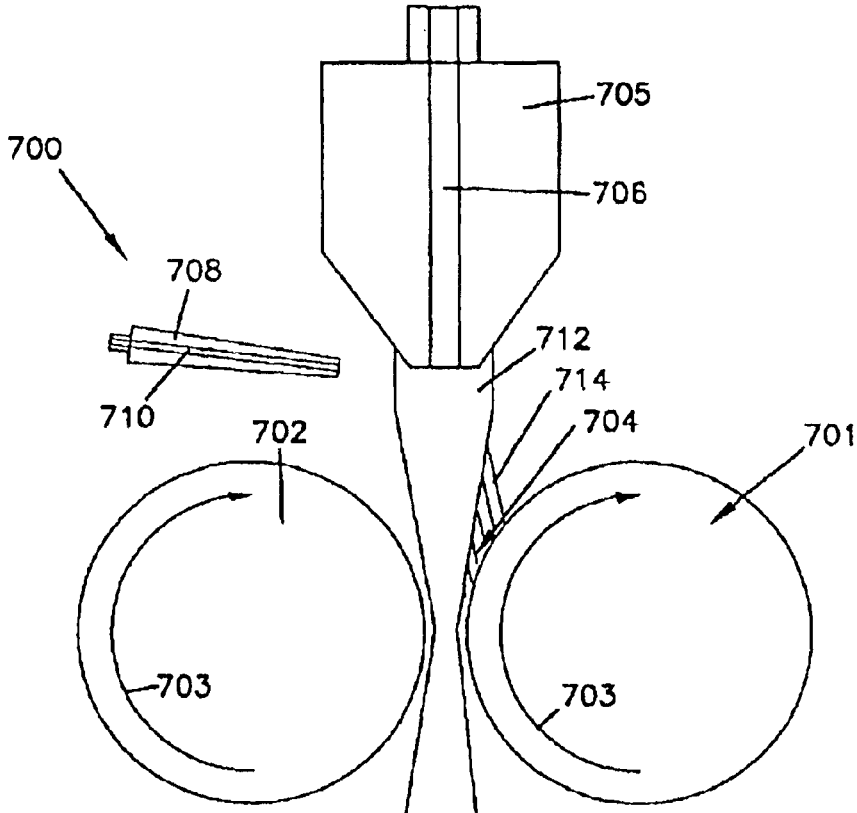
FIG. 29

METHOD AND APPARATUS FOR COATING OF SUBSTRATES

Matter enclosed in heavy brackets [ ] appears in the original patent but forms no part of this reissue specification; matter printed in italics indicates the additions made by reissue.

This application [claims priority of] *is a Continuation-in-Part of* U.S. patent application Ser. No. 10/256,349, filed Sep. 27, 2002, *now U.S. Pat. No. 7,192,484,* which application is incorporated herein by reference.

FIELD OF THE INVENTION

The invention relates to methods and apparatuses for coating a device. The invention relates to methods and apparatuses that reduce problems encountered during coating of a device, such as a medical device having a cylindrical shape.

BACKGROUND OF THE INVENTION

Medical devices are becoming increasingly complex in function and geometry. It has been recognized that imparting desirable properties to the surface of medical devices, in particular small implantable medical devices, by coating the surface of the device with one or more compounds can enhance the function and effectiveness of the medical device. Traditional coating methods, such as dip coating, are often undesirable for coating these complex geometries since coating solution may get entrapped in the device structure. This entrapped solution may cause webbing or bridging of the coating solution and may hinder the device from functioning properly.

Other techniques, such as spray coating, have also been used to apply coating material to various devices, including medical devices. However, some methods of spray coating can also be problematic. In particular, devices may stick to components of the coating apparatus. Sticking may cause problems manipulating the devices and may result in an increased defect rate. Further, devices to be coated may have or pick up a static charge. A static charge may also lead to problems in manipulating the devices and may also result in an increased defect rate. Problems with sticking and static charges can be greater in the context of stents that are small in size.

Accordingly, there is a need for methods and devices for overcoming problems associated with spray coating procedures.

SUMMARY

The invention relates to methods and an apparatus that reduce problems encountered during coating of a device, such as a medical device having a cylindrical shape. In an embodiment, the invention includes an apparatus for coating a surface of a device having a device rotator which includes at least one pair of rollers, each pair comprising a first roller and a second roller. The first and second rollers can be separated by a gap. The apparatus can also include a spray nozzle able to produce a spray of a coating material in a pattern, wherein the spray nozzle is arranged to direct its spray at the gap, and an indexing system configured to control the device rotator to rotate the pair of rollers in a first direction a first amount of rotation and then in a second direction a second amount of rotation, the first direction being opposite of the second direction.

In an embodiment, the invention includes a method for coating a rollable or round medical device including the steps of placing a medical device on a device rotator, the device rotator comprising a pair of rollers, the pair comprising a first roller and a second roller, the first and second rollers separated by a gap not wider than the device, disposing a coating material on the medical device, including spraying a coating material from a nozzle, wherein the nozzle is arranged to direct spray at the gap. The method can also include rotating the medical device a first amount of rotation by rotating at least one of the first or second rollers in a first direction, and rotating the medical device a second amount of rotation by rotating at least one of the first or second rollers in a second direction, the first direction being opposite of the second direction.

In an embodiment, the invention includes an apparatus for coating a surface of a medical device comprising a device rotator having at least one pair of rollers, each pair having a first roller and a second roller, wherein the first and second rollers are separated by a gap, a sonicating spray nozzle, and a coating solution supply conduit, the coating solution supply member having a major axis oriented parallel to the gap.

In an embodiment, the invention includes an apparatus for coating a surface of a medical device having a device rotator containing at least one pair of rollers, each pair having a first roller and a second roller, wherein the first and second rollers are separated by a gap, a spray nozzle able to produce a spray of a coating material in a pattern, wherein the spray nozzle is arranged to direct its spray at the gap, a spray nozzle support member attached to the spray nozzle, and a device retaining member disposed at a distance from at least one of the rollers that is less than the diameter of the medical device.

In an embodiment, the invention includes an apparatus for coating a surface of a medical device having a device rotator including at least one pair of rollers, each pair having a first roller and a second roller, wherein the first and second rollers are separated by a gap, a spray nozzle able to produce a spray of a coating material in a pattern, wherein the spray nozzle is arranged to direct its spray at the gap, a spray nozzle support member attached to the spray nozzle, and an air nozzle adapted and configured to direct a stream of air at at least one of the first and second rollers.

In an embodiment, the invention includes a method for coating small diameter medical devices including the steps of removing a static charge from a small diameter medical device, placing the small diameter medical device on a device rotator, the device rotator comprising a pair of rollers, the pair including a first roller and a second roller separated by a gap not wider than the device, and disposing a coating material on the small diameter medical device, including spraying a coating material from a nozzle, wherein the nozzle is arranged to direct spray at the gap.

BRIEF DESCRIPTION OF THE DRAWINGS

FIG. 1 is a schematic cross-sectional view of a coating apparatus in accordance with an embodiment of the invention.

FIG. 2 is a schematic cross-sectional view of a coating apparatus showing a rollable device moving out of a gap between two rollers.

FIG. 19 is a schematic cross-sectional view of a coating apparatus having rollers with a bi-directional indexing movement.

FIG. 20 is a schematic cross-sectional view of a coating apparatus in accordance with an embodiment of the invention.

FIG. 21 is a schematic cross-sectional view of a coating apparatus in accordance with an embodiment of the invention having a device retaining member.

FIG. 22 is a schematic cross-sectional view of a coating apparatus in accordance with an embodiment of the invention showing a rollable device contacting a device retaining member.

FIG. 26 is a schematic cross-sectional view of a coating apparatus in accordance with an embodiment of the invention having an air nozzle directing a stream of air at a rollable device.

FIG. 29 is a schematic cross-sectional view of a coating apparatus in accordance with an embodiment of the invention having a solution delivery member arranged in a first configuration.

DETAILED DESCRIPTION OF THE INVENTION

Figure 3:
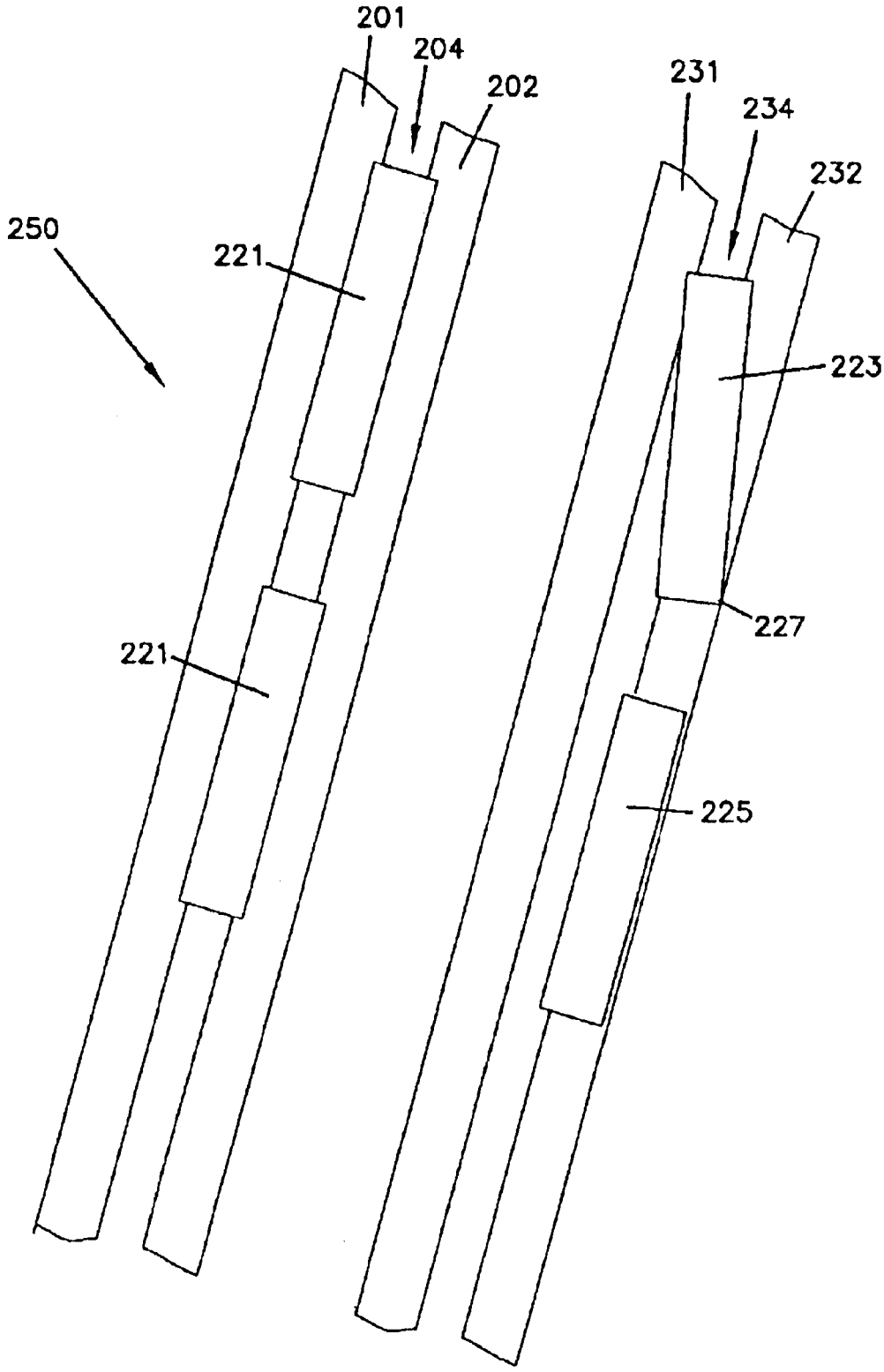
FIG. 3 is a top view of rollable devices positioned in a gap between two rollers and rollable devices moving out of a gap between two rollers.

Spray coating techniques are commonly used to apply coating material to various devices, including medical devices. However, during the spray coating process, devices may stick or adhere to components of the coating apparatus. While not intending to be bound by theory it is believed that the sticking is, in part, due to coating spray causing adhesion between components of the coating apparatus and the device to be coated. It is also believed that the sticking is, in part, due to electrostatic attraction and repulsion as the device to be coated can have or pick up a static charge.

Problems with sticking and static charges can be greater in the context of devices to be coated that are small in size. While not intending to be bound by theory, it is believed that sticking and static charges can cause greater problems with small devices simply because small devices have less mass. That is, all other factors applied equally, it takes less force to act on a smaller mass than a larger mass. In an embodiment of the invention, devices with a diameter of less than 2.0 millimeters can be coated. Devices with a diameter of less than 1.5 millimeters can also be coated.

Both mis-deposited coating spray and static charges can lead to coating problems. By way of example, referring to FIG. 1, in a spray coating system 200 that has a pair of rollers 201, 202, a device 203 to be coated is normally positioned in the gap 204 between the rollers. A spray head 215 creates a spray stream 217 that is applied to the device 203. Where the device does not have a continuous surface, an amount of spray 219 may pass between the rollers. However, some amount of spray (not shown) can be laterally deflected after hitting the device 203 and may be deposited onto one or both of the pair of rollers 201, 202. In addition, depending on how the spray head 215 is arranged, some of the overspray 219 can be deposited on one or both of the rollers, instead of simply passing between the rollers 201, 202. The spray that is deposited onto the rollers 201, 202 may lead to sticking between the device and the rollers 201, 202. Finally, as discussed above, the device 203 may have or pick up a static charge. This static charge may cause the device 203 to be attracted to, or repulsed by, other components of the coating apparatus, such as the rollers 201, 202, depending on the charge they carry.

The rollers 201, 202 rotate in order to expose different sides of the device 203 to the spray stream 217. Referring now to FIG. 2, where sticking occurs, the device 203 may stick to a roller 202 and be moved out of the gap 204 when the rollers are rotated. Specifically, the device 203 may move in the direction of arrow 209, or one end of the device may move in the direction of arrow 209. Misdeposited coating spray, static charges, or a combination of both may cause the sticking.

Referring now to FIG. 3, two devices 221 are shown in the proper position disposed in the gap 204 between a pair of rollers 201, 202. Two more devices 223, 225, are shown out of position with respect to another pair of rollers 231, 232. Device 223 has one end 227 that has rolled up onto roller 232. Both ends of device 225 have rolled up onto roller 232. Devices 223, 225 may have moved out of position because of sticking problems associated with coating spray, static charges, or both. Embodiments of the present invention include methods and devices for overcoming problems associated with spray coating.

In an embodiment, the invention includes an apparatus for coating a surface of a device having a device rotator including at least one pair of rollers, each pair comprising a first roller and a second roller. The first and second rollers can be separated by a gap. The apparatus can also include a spray nozzle able to produce a spray of a coating material in a pattern, wherein the spray nozzle is arranged to direct its spray at the gap, and an indexing system configured to control the device rotator to rotate the pair of rollers in a first direction a first amount of rotation and then in a second direction a second amount of rotation, the first direction being opposite of the second direction.

In an embodiment, the invention includes a method for coating a rollable medical device including the steps of placing a medical device on a device rotator, the device rotator comprising a pair of rollers, the pair comprising a first roller and a second roller, the first and second rollers separated by a gap not wider than the device, disposing a coating material on the medical device, including spraying a coating material from a nozzle, wherein the nozzle is arranged to direct spray at the gap. The method can also include rotating the medical device a first amount of rotation by rotating at least one of the first or second rollers in a first direction, and rotating the medical device a second amount of rotation by rotating at least one of the first or second rollers in a second direction, the first direction being opposite of the second direction.

In an embodiment, the invention includes an apparatus for coating a surface of a medical device comprising a device rotator having at least one pair of rollers, each pair having a first roller and a second roller, wherein the first and second rollers are separated by a gap, a sonicating spray nozzle, and a coating solution supply conduit, the coating solution supply member having a major axis oriented parallel to the gap, or in the same plane as the gap.

In an embodiment, the invention includes an apparatus for coating a surface of a medical device having a device rotator containing at least one pair of rollers, each pair having a first roller and a second roller, wherein the first and second rollers are separated by a gap, a spray nozzle able to produce a spray of a coating material in a pattern, wherein the spray nozzle is arranged to direct its spray at the gap, a spray nozzle support member attached to the spray nozzle, and a device retaining member disposed at a distance from at least one of the rollers that is less than the diameter of the medical device.

In an embodiment, the invention includes an apparatus for coating a surface of a medical device having a device rotator including at least one pair of rollers, each pair having a first roller and a second roller, wherein the first and second rollers are separated by a gap, a spray nozzle able to produce a spray of a coating material in a pattern, wherein the spray nozzle is arranged to direct its spray at the gap, a spray nozzle support member attached to the spray nozzle, and an air source, such as an air knife, adapted and configured to direct a stream of air at one or both of the first and second rollers.

In an embodiment, the invention includes a method for coating small diameter medical devices including the steps of removing a static charge from a small diameter medical device, placing the small diameter medical device on a device rotator, the device rotator comprising a pair of rollers, the pair including a first roller and a second roller separated by a gap not wider than the device, and disposing a coating material on the small diameter medical device, including spraying a coating material from a nozzle, wherein the nozzle is arranged to direct spray at the gap.

One aspect of the present invention relates to an apparatus for coating a rollable device, the apparatus including a pair of rollers and a spray nozzle. The pair of rollers, which include a first roller and second roller are rotatable and are arranged substantially parallel to each other and are separated by a gap. The pair of rollers can support and rotate one or more rollable devices to be coated. A rollable device is typically positioned on the rollers between the tip of the spray nozzle and the gap between the rollers. Since the rollable device is positioned over the gap, the gap is generally not larger than the diameter of the rollable device. "Rollable device" or "device" refers to any sort of object that can receive a spray coating and that can be held in position by the pair of rollers and rotated in place. Rollable devices can have a cylindrical or tubular shape and can be rotated about the axis of the pair of rollers. Cylindrical may include those shapes only generally cylindrical. By way of example, cylindrical may include polygonal. Substantially parallel includes those configurations where two objects are not exactly parallel to each other. By way of example, substantially parallel can include the circumstance where two objects have an angle between them of less than 10 degrees. Substantially parallel can also include the circumstance where two objects have an angle between them of less than 15 degrees.

The spray nozzle is configured to produce a spray of a coating material that is directed towards the gap between the rollers. When the spray nozzle is actuated and when the device is positioned on the rollers, at least a portion of the device is coated with the coating material. In one aspect of the invention, the coating nozzle is configured to produce a spray having a narrow spray pattern. As used herein, "spray pattern" refers to the shape of the body of coating material sprayed from the spray nozzle, wherein the shape of the spray pattern is independent of the presence of the rollers. "Spray" or "sprayed material" refers to the droplets of coating material that are produced from the spray nozzle.

In one embodiment of the invention, a majority of the sprayed coating material is passed through the gap, the amount of passed material amount being measured when the device is not positioned on the pair of rollers. In another embodiment, the spray nozzle is configured to produce a spray of coating material having a spray pattern wherein the width of the spray pattern at the gap that is not greater than 150% of the width of the gap. According to these embodiments, a device positioned on the rollers can receive a portion of the sprayed coating material, be rotated, and receive subsequent applications of the coating material as needed. The majority of the coating material that is not deposited on the device generally passes through the gap. A smaller amount of a coating material may get deposited on the rollers. For example, when a device having perforations or openings is coated, some coating material will pass through the device. A majority of the sprayed coating material that passes through the device will also pass through the gap between the rollers.

In one embodiment, the spray nozzle is angled relative to the first axis or second axis. That is, the spray nozzle is tilted so that the sprayed material is delivered at an angle relative to the axis of the rollers. The angle is less than 90° but more than 5° relative to the axis of the rollers. This arrangement is particularly useful when coating devices that have openings, as a greater amount of the sprayed coating material can be deposited on the surface of the device rather than being passed through the device and through the gap.

For some devices, such as devices having a cylindrical or tubular shape, a coating process typically involves applying the coating material multiple times (i.e., multiple applications of a coating material) on the device, wherein each time a different portion of the device receives an application of the coating material. Often, the same or overlapping portions of the device are coated multiple times in order to produce a device having a desired quality or quantity of coating material. Generally, after a portion of the device is coated with a first application of a coating material, the rollers are rotated, for example, by an indexing function, thereby rotating the device to a position for a subsequent application of a coating material.

The device can be coated and rotated until a desired coating is achieved. The apparatus is particularly suitable for coating rollable devices having complex surface geometries, for example, medical devices such a stents having multiple sections, or other rollable devices that include webbed-like structures, or that have spaces, apertures, openings, or voids.

In one aspect, the apparatus and the methods described herein allow for a "wet coating" method. Wet coating involves disposing the coating material on a portion of the device and then rotating the device on the rollers, placing the coated portion of the device in contact with the rollers prior to the coating material drying on the coated portion of the device. "Dry" or "dried" refers to the condition of the coated portion of the devices, wherein the coated portion is not tacky and wherein most of any solvent in the coated portion has evaporated from the device surface. The current apparatus and methods described herein provide a significant improvement in spray coating, as previous coating processes typically require that the coating is dried before the device is manipulated.

In one embodiment of the invention, the spray nozzle is movable. More specifically, the spray nozzle is movable in a direction parallel to the axis of the first or second roller. The nozzle can be moved along the axis while applying a coating to one or more devices that are positioned on the pair of rollers, thereby resulting in a portion of one or more devices being coated. For example, the spray nozzle can provide a coating material to a portion of a device having a cylindrical shape while moving along the roller axis allowing for a "stripe" of coating material to be deposited along a portion of the length of the device. The stripe of deposited coating material has a width that is typically a fraction of the circumference of the device. The device can be rotated as desired and the step of depositing coating material can be repeated. According to the arrangement of the nozzle having a spray pattern and the pair of rollers having the gap, the majority of the coating material that does not get deposited on the device is passed through the gap between the rollers.

These arrangements allow for the improved spray coating of a rollable device, particularly when the device is positioned, coated, and rotated with the spray coating apparatus as described herein. These improvements can been seen, for example, in the uniformity of the applied coating, the consistency in the amount of applied coating, and the rate that the coating material can be applied to a device. A substantial improvement in coating is observed as compared to traditional coating apparatus or other spray coating arrangements.

In order to describe the invention in greater detail, reference to the following illustrations are made. The illustrations are not intended to limit the scope of the invention in any way but are to demonstrate some of the various embodiments of the coating apparatus and its features. Elements in common among the embodiments shown in the figures are numbered identically and such elements need not be separately discussed.

Figure 4:
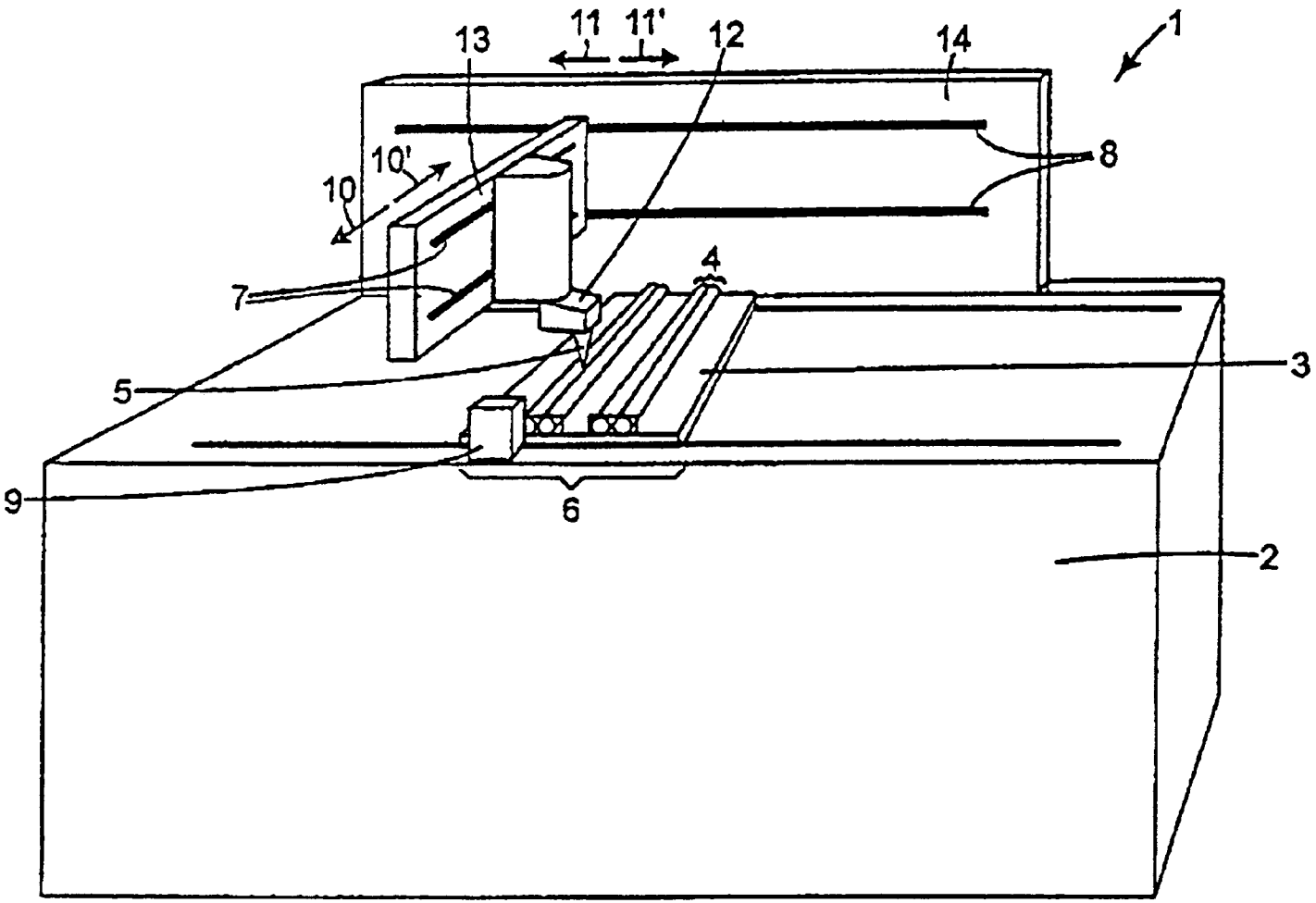
FIG. 4 is an illustration of one embodiment of the coating apparatus.

In one embodiment, the coating apparatus includes a device rotator having at least one pair of rollers which includes a first roller and second roller, a gap between the first and second rollers, and a spray nozzle producing a spray pattern directed at the gap. As illustrated in FIG. 4, the coating apparatus 1 according to the invention can include a housing 2 on which the coating process is performed. A tray 3 having one or more pairs of rollers 4 can be positioned on the top of the housing 2. Tray 3 can be brought into the proximity of a spray nozzle 5. Now referring to FIG. 6, which illustrates the tray 3 in greater detail, the pair of rollers 4 includes a first roller 31 and a second roller 32 (also referred to as "roller" or "rollers") which are arranged substantially parallel to each other and mounted on tray 3 by bracket 33. Now referring to FIG. 10, which also shows the pair of rollers 4 in greater detail, gap 70 separates the first roller 31 and the second roller 32.

Gap 70 is maintained at a constant width along the entire length of the pair of rollers. Gap 70 also has a width that is less than the size of the device (i.e., typically the diameter of a device having a cylindrical shape) to be coated. In most arrangements gap 70 is less than 5 cm. In some preferred embodiments gap 70 is less than 10 mm wide and, more preferably, less than 2.5 mm wide. In one particularly preferred embodiment, the gap is in a range of 0.1 mm to 2.5 mm wide.

Figure 5:
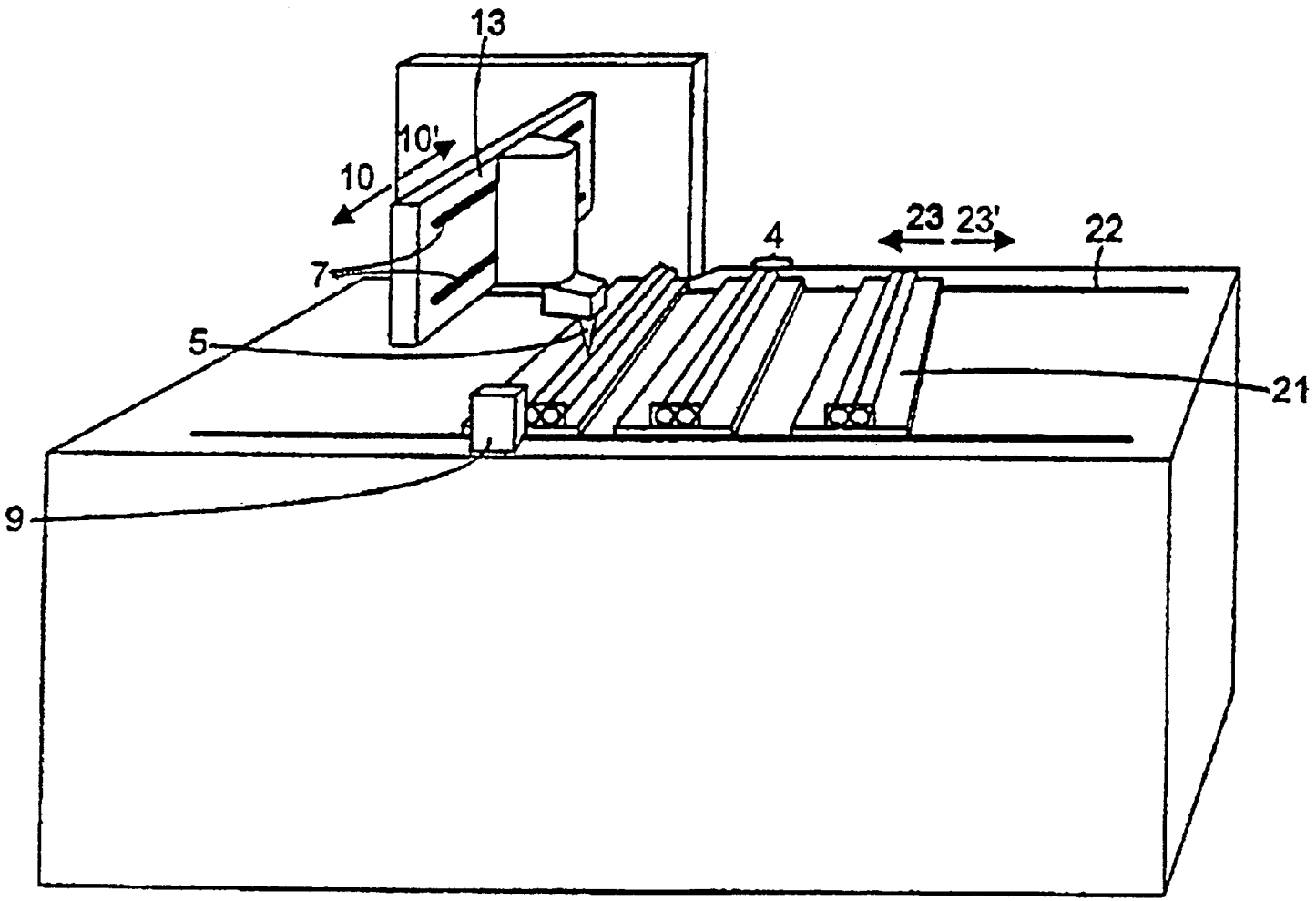
FIG. 5 is an illustration of another embodiment of the coating apparatus.

Referring back to FIG. 6, first roller 31, second roller 32, or both, are rotatable in either direction as indicated by arrows 34 or 34'. Typically, the first roller 31 and the second roller 32 are rotatable in the same direction. Bracket 33 can also include a fastening mechanism, such as a screw, pin, or clamp, which keeps the bracket 33 together and secures the first roller 31 and second roller 32 to the tray 3. The fastening mechanism of the bracket 33 can be loosened to uncouple the bracket 33 and allow removal and replacement of the rollers. Tray 3 can include any number of pairs of rollers 4. For example, the tray could include two pair of rollers as illustrated in FIG. 4 or one pair of rollers as illustrated in FIG. 5.

The rollers can be of any length or circumference, but preferably have a length in the range of 1 cm–1000 cm and more preferably in the range of 5 cm–100 cm. The rollers preferably have a circumference is in the range of 1 mm–100 cm, and more preferably in the range of 5 mm–100 mm. Rollers can be fabricated according to the size and the desired number of the devices to be coated during the coating process. The diameter of the rollers can either be larger or smaller than the diameter of the device to be coated.

The rollers can be made of any suitable durable material, for example, stainless steel, polypropylene, high density polyethylene, low density polyethylene, or glass. Optionally the rollers can be coated with non-stick materials, including, but not limited to, compounds such as tetrafluoroethylene (TFE); polytetrafluoroethylene (PTFE); fluorinated ethylene propylene (FEP); perfluoroalkoxy (PFA); fluorosilicone; and other compositions such as silicone rubber.

Figure 7:
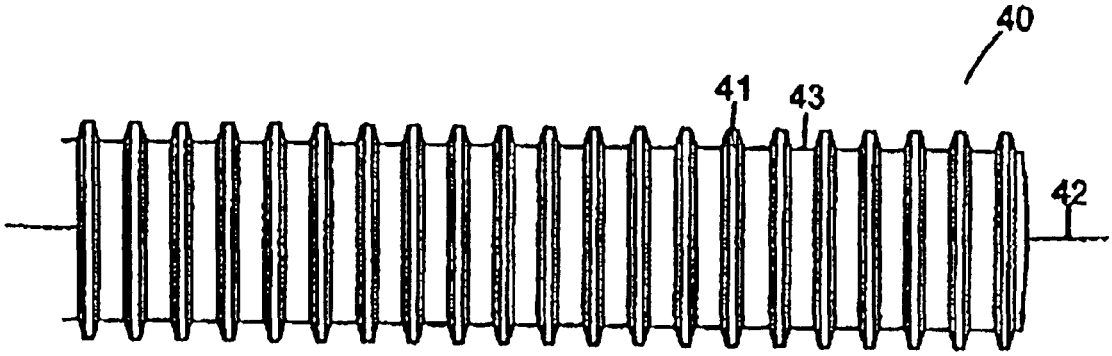
FIG. 7 is an illustration of a roller having rib structures.

In another embodiment, the coating apparatus includes a device rotator having at least one pair of rollers, and either, or both, the first and second roller includes at least one of rib-like structure, herein referred to as "ribs". Ribs refer to any sort of raised portion around the circumference of the roller. As illustrated in FIG. 7, roller 40 is shown having plurality or ribs 41. The ribs 41 of the roller 40 are typically spaced along the length of the roller 40 and can be an integral part of the roller itself. For example, and in a preferred embodiment, the ribs 41 are molded around the central portion of the roller. Alternatively, the ribs 41 can be formed by placement of O-rings or bands around a rod, such as a metal rod, which is the central portion of the roller. Generally, the ribs 41 are arranged perpendicular to the central axis 42 of the roller 40 and are spaced by a non-ribbed surface 43 of the roller 40. The ribs 41 can be spaced in any manner, for example, evenly, or unevenly.

Figure 8:
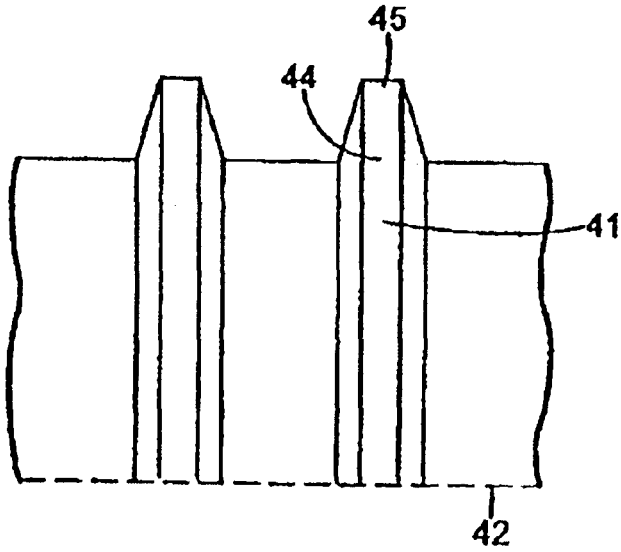
FIG. 8 is an illustration of the rib portion of a roller having rib structures.

In a preferred embodiment, referring to FIG. 8, the ribs 41 of the roller have a wider portion 44 proximal to the central axis 42 of the roller 40, and a narrower portion 45 distal to the central axis 42 of the roller. The gradual narrowing of the rib 41 further from the central axis can be exemplified in a variety of shapes. For example, rib 41 can have a triangular shape or tapered shape. Other rib shapes, for example, trapezoidal shapes or shapes that include curved surfaces and that provide a shape that is wider proximal to the central axis 42 of the roller 40 and narrower distal to the central axis 42 of the roller are also contemplated.

In one aspect of the invention, the narrower portion 45 of the ribs 41 can be in contact with the device when the device is positioned on the pair of rollers. Generally, the narrower portion 45 of the rib 41 provides minimal surface contact with a device yet allows the device to be rotated by rotation of either the first or second roller. The ribs 41 can be spaced along the roller 40 in any manner but typically are arranged to provide at least three device contact points for each pair of rollers. For example, two ribs on each roller, or, where the ribs on adjacent rollers are offset from each other, two ribs of the first roller and one rib of the second roller contact the device. According to the invention, the ribs can be spaced in the range of 1 rib/0.1 mm to 1 rib/10 cm along the length of the roller, and more preferably in the range of 1 rib/mm to 1 rib/20 mm along the length of the roller.

Figure 9:
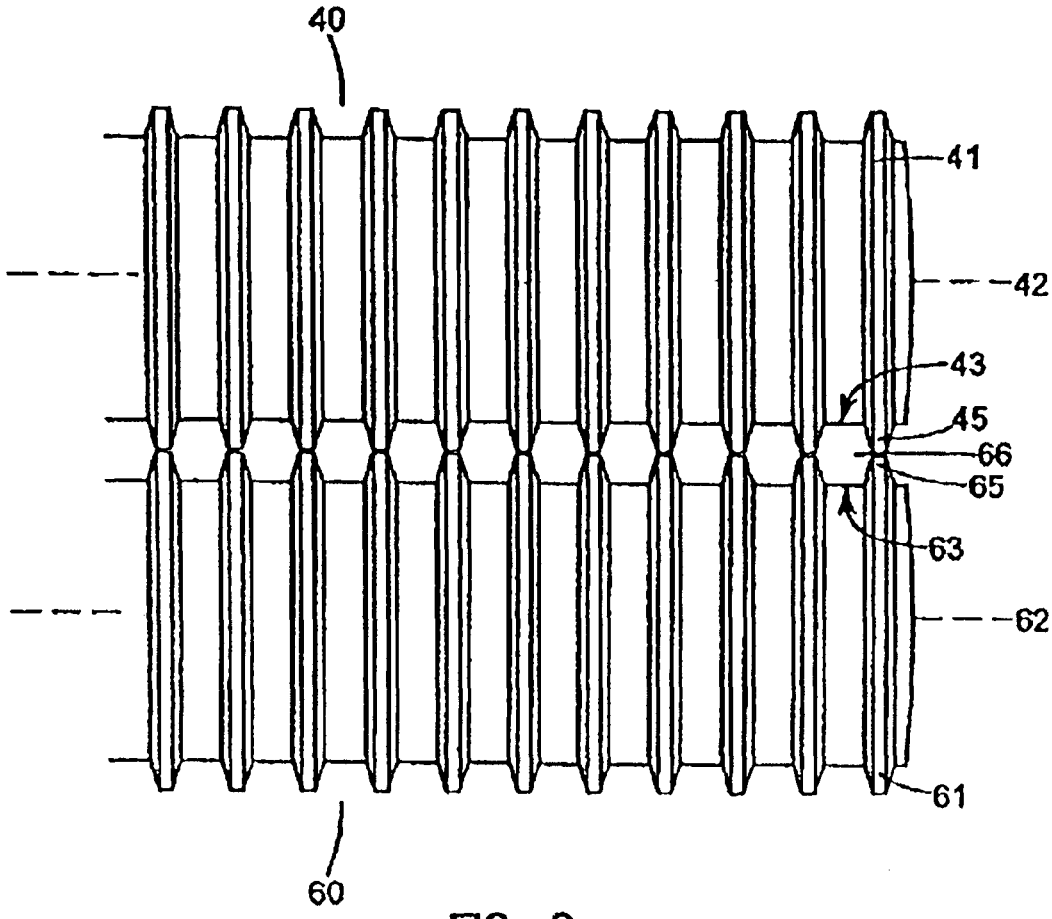
FIG. 9 is an illustration of a pair of rollers having rib structures.

In one embodiment, as illustrated in FIG. 9, a pair of rollers includes a first roller 40 having a plurality of first roller ribs 41 and a second roller 60 having a plurality of second roller ribs 61, and wherein the first roller 40 and second roller 60 are substantially parallel to each other. In one aspect, the first roller ribs 41 and the second roller ribs 61, which are generally perpendicular to the first roller axis 42 and second roller axis 62, respectively, are aligned with each other. In this aspect, the narrower portion 45 of the first roller rib 41 is adjacent to a narrower portion 65 of the second roller rib 61. The distance between the narrower portion 45 and the narrower portion 65 can be small, but spaced to allow the first roller 40 and the second roller 60 to rotate freely. In this embodiment, a gap 66 exists between the first roller 40 and second roller 60, primarily between non-ribbed surface 43 of roller 40 and non-ribbed surface 63 of roller 60. Accordingly, the area of gap 66 is sufficient to allow the majority of the sprayed coating material (not shown), which is generally directed between the first roller 40 and second roller 60, to pass through the gap 66, which includes any space between the narrower portion 45 and the narrower portion 65.

In other embodiments, alignment of the first roller ribs 41 and the second roller ribs 61 is offset. In these embodiments a distance between the first roller 40 and the second roller 60 is maintained to allow for a gap of sufficient size to allow the majority of the sprayed coating material to pass through the gap.

It is understood that the gap between a first roller having a plurality of ribs and a second roller having a plurality of ribs can be of any shape or area sufficient to provide and arrangement wherein the majority of the sprayed coating material passes through the gap.

Figure 10:
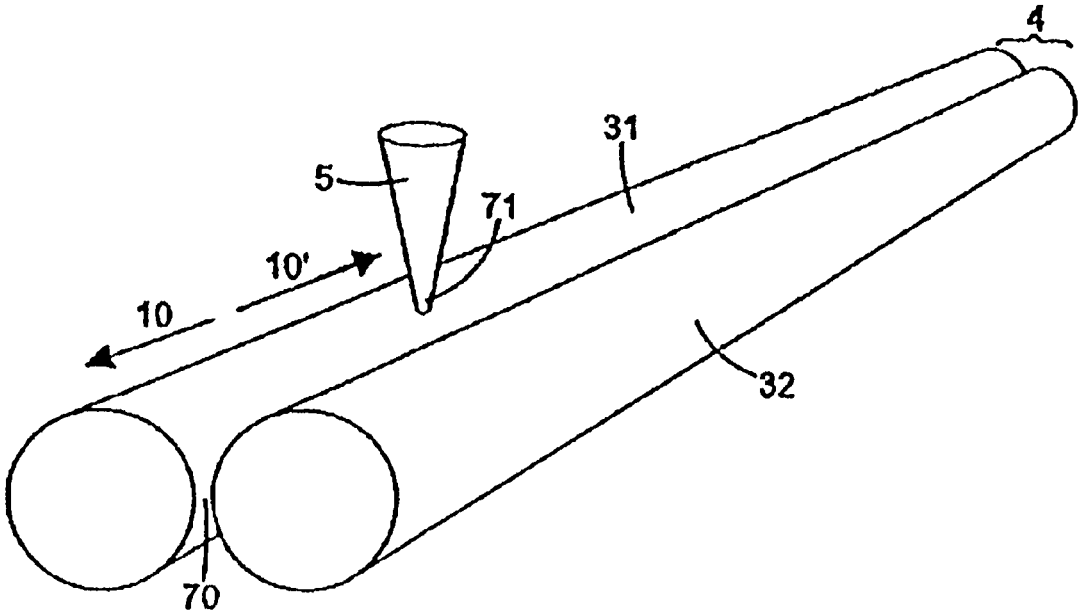
FIG. 10 is an illustration of a pair of rollers and a portion of a spray nozzle.

In one embodiment, as illustrated in FIG. 10, the first roller 31 and second roller 32 have a circular shape. However, the rollers can be of any suitable shape that allows rotation of the device on the rollers. For example, the circumference of the rollers can have flat surfaces and can be, for example, polygonal in shape. If the rollers have a polygonal shape it is preferable that there are a sufficient number of sides to cause rotation of the device on the rollers.

According to the invention, and referring to FIG. 10, prior to an application of a spray coating on the device, gap 70, between the first roller 31 and the second roller 32 is aligned with the tip 71 of the spray nozzle 5. Now referring to FIG. 12, which shows a different view of the nozzle and rollers, the tip 71 of the spray nozzle 5 is aligned with the gap 70. Alignment refers to positioning the spray nozzle 5 so that the spray of coating material 90 is directed towards the gap 70. As shown, the alignment allows the majority of the spray of coating material 90 to pass through gap 70. The spray of coating material 90 is generally directed at the gap 70, however, to a limited extent, the spray of coating material 90 can also come into contact with a portion of the first roller 31 and second roller 32.

The distance from the tip 71 of the spray nozzle 5 to the gap 70 can be arranged according to the size of the device to be coated. In one embodiment, the distance from the tip 71 of the spray nozzle 5 to the gap 70 is in the range of 1 mm–15 mm. More preferably, distance from the tip 71 of the spray nozzle 5 to the gap 70 is in the range of 1 mm–7.5 mm.

Figure 12:
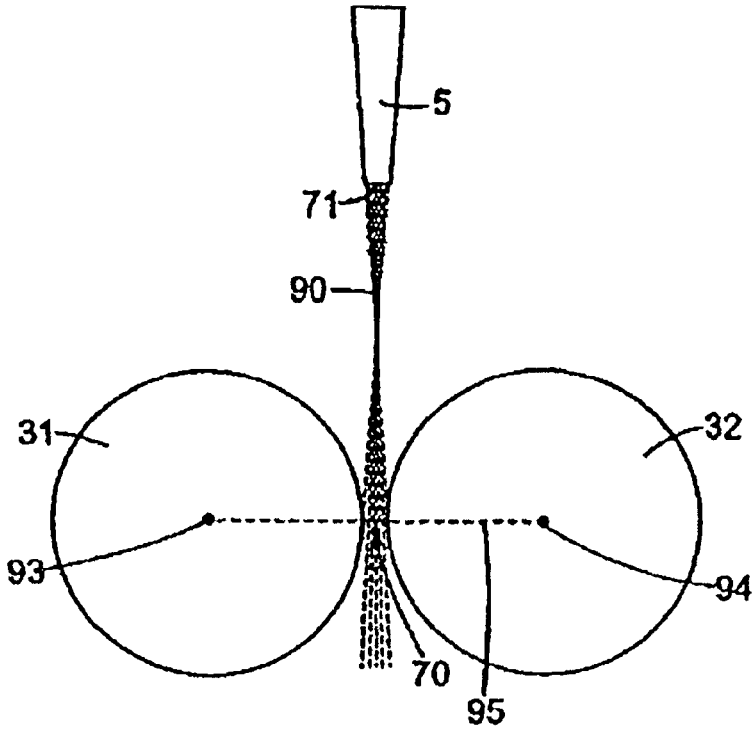
FIG. 12 is an illustration of one embodiment of the spray nozzle having a spray pattern and a pair of rollers.

Various configurations of the spray nozzle and the first and second rollers are contemplated. In one embodiment, as illustrated in FIG. 12, the first roller 31 and second roller 32 have the same circumference, are horizontally level (i.e., line 95 connecting a point on the first axis 93 and a point on the second axis 94 is parallel to the horizontal), and is separated by a gap 70. In this embodiment the sprayed coating material 90 is directed from the tip 71 of the nozzle 5 towards the gap 70 and is generally perpendicular to line 95. The majority of the sprayed coating material 90 passes through gap 70 (as shown without device on the rollers).

Figure 16:
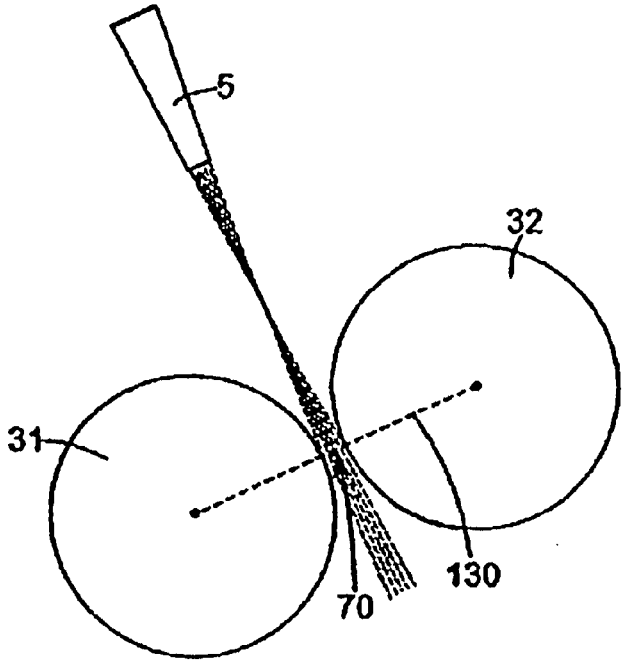
FIG. 16 is an illustration of another embodiment of a spray nozzle having a spray pattern and a pair of rollers.

In another embodiment of the invention, as illustrated in FIG. 16, the first roller 31 and the second roller 32 have the same circumference and are separated by a gap 70 but are not horizontally level with each other. Line 130 is not parallel with the horizon but is at an angle generally less than 90° relative to the horizon. Nozzle 5 is arranged to provide a spray pattern 90 so that is directed towards the gap and generally perpendicular to the line 130.

Figure 17:
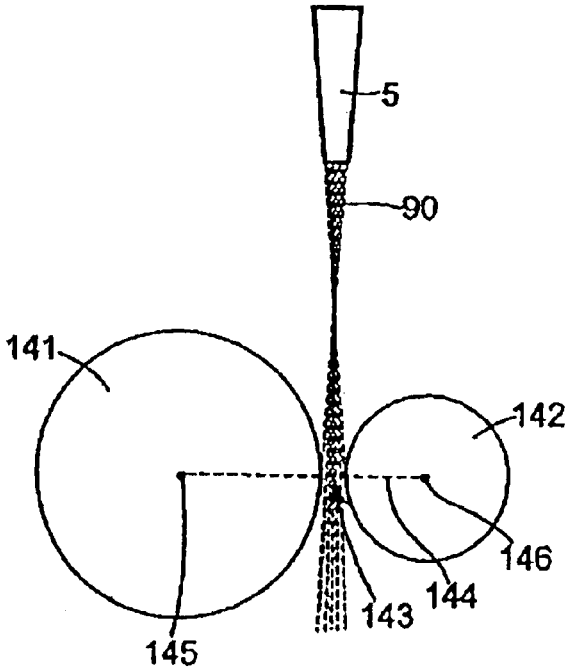
FIG. 17 is an illustration of another embodiment of a spray nozzle having a spray pattern and a pair of rollers.

In another embodiment of the invention, as illustrated in FIG. 17, the first line 141 and second 142 rollers have a different circumference, are separated by a gap 143, and are horizontally level (i.e., according to line 144, established by first axis point 145 and second axis point 146). In this embodiment the sprayed coating material 90 from nozzle 5 is directed towards the gap 70 and is generally perpendicular to line 144.

Figure 13:
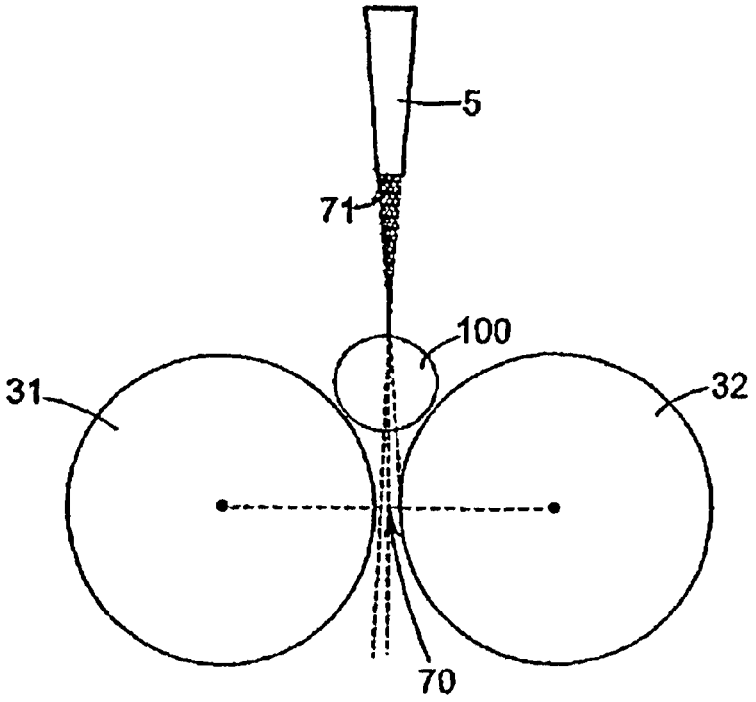
FIG. 13 is an illustration of one embodiment of the spray nozzle having a spray pattern, a pair of rollers, and with a rollable device.
Figure 14:
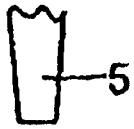
FIG. 14 is an illustration of a portion of a rollable device that has been coated with a coating solution.
Figure 14:
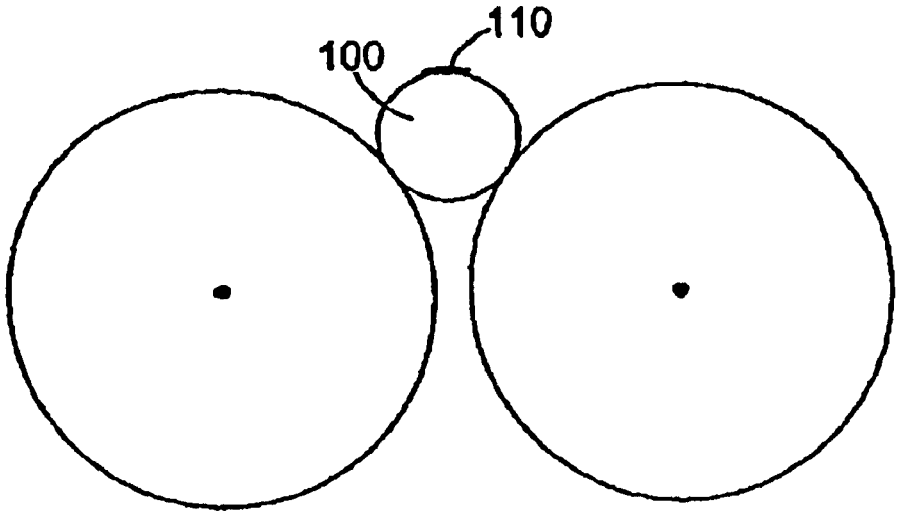

During use of the coating apparatus, referring to FIG. 13, device 100 is positioned on the pair of rollers, contacting the first roller 31 and second roller 32. The device 100 is situated between the tip 71 of the spray nozzle 5 and gap 70. A portion of the device, proximal to the tip 71, receives at least a portion of the sprayed coating material 90. Generally, now referring to FIG. 14, a portion of the device 100 will have a stripe 110 of coating material applied after a first coating application.

Often, referring back to FIG. 13, device 100 will not have a contiguous surface (i.e., will have perforations or a webbed structure). During the step of providing a coating to the device 100, some of the sprayed material passes through openings in the device 100. The majority of the spray that passes through the device 100 (i.e., that does not adhere to the device), also passes through gap 70 between the first roller 31 and the second roller 32.

As previously stated, the spray pattern refers to the general shape of the body of sprayed material absent the rollers. In order to describe aspects of the invention, the spray pattern, for example, the spray pattern 90 as illustrated in FIG. 12, has a width at line 95 (the location of gap 70) that is wider than gap 70. In one embodiment of the invention, the width of the spray pattern at the gap is not greater than 150% of the width of the gap. In other arrangements, the width of the spray pattern is narrower and is not greater than 125% of the width of the gap. The width of the spray pattern at the gap can be determined by, for example, a) determining the distance from the tip 71 of the nozzle 5 to the line 95, b) removing both the first roller 31 and second roller 32, c) providing a spray of coating material to a flat surface, such as a piece of paper on a platform, for collection of the sprayed coating material, the paper set the distance from the tip 71 determined in step a), d) determining the width of the applied spray on the flat surface, and then e) comparing the width of the spray on the paper as determined in step d) to the width of the gap 70.

In another embodiment of the invention, the apparatus is arranged so the majority of the spray passes through the gap. In some arrangements, at least 75% of the spray passes through the gap; in other arrangements at least 90% of the spray passes through the gap; and yet in other arrangements at least 95% of the spray passes through the gap. In order to determine if a coating apparatus meets these requirements, a similar approach to measuring can be taken. For example, a flat surface, such as a piece of paper on a platform, can be used to collect the coating material sprayed. A paper can be placed directly below the gap to collect spray that passes through the gap. The first and second roller can then be removed and another paper (for collection of the total spray) can be placed at the same distance to collect the total spray from the spray nozzle under the same spray conditions. The papers can then be weighed to determine the amount of coating and then compared. According to the invention, the amount of coating material that passes through the gap is at least 50% of the total coating material sprayed.

Figure 15:
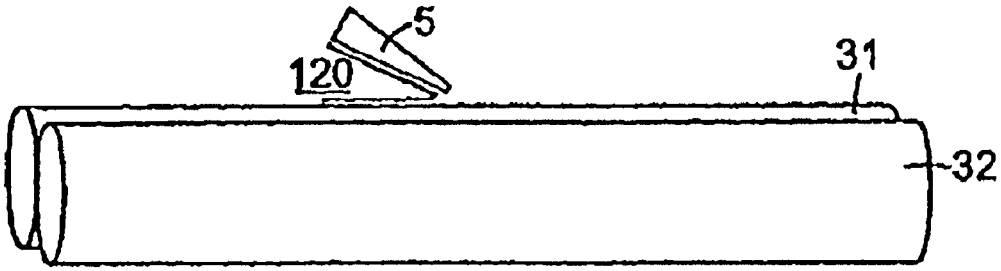
FIG. 15 is an illustration of a pair of rollers and a portion of a spray nozzle that is angled relative to the axis of the rollers.

In one embodiment of the invention, the spray nozzle is angled relative to the first axis or second axis. As illustrated in FIG. 15, spray nozzle 5 is tilted so that the sprayed material is delivered at an angle 120 relative to the axis of the first roller 31 or second roller 32. Angle 120 is less than 90° but more than 5° relative to the axis of the rollers. This arrangement is particularly useful when coating devices that have openings as a greater amount of the sprayed coating material can be deposited on the surface of the device rather than passing through the device and through the gap.

Figure 18:
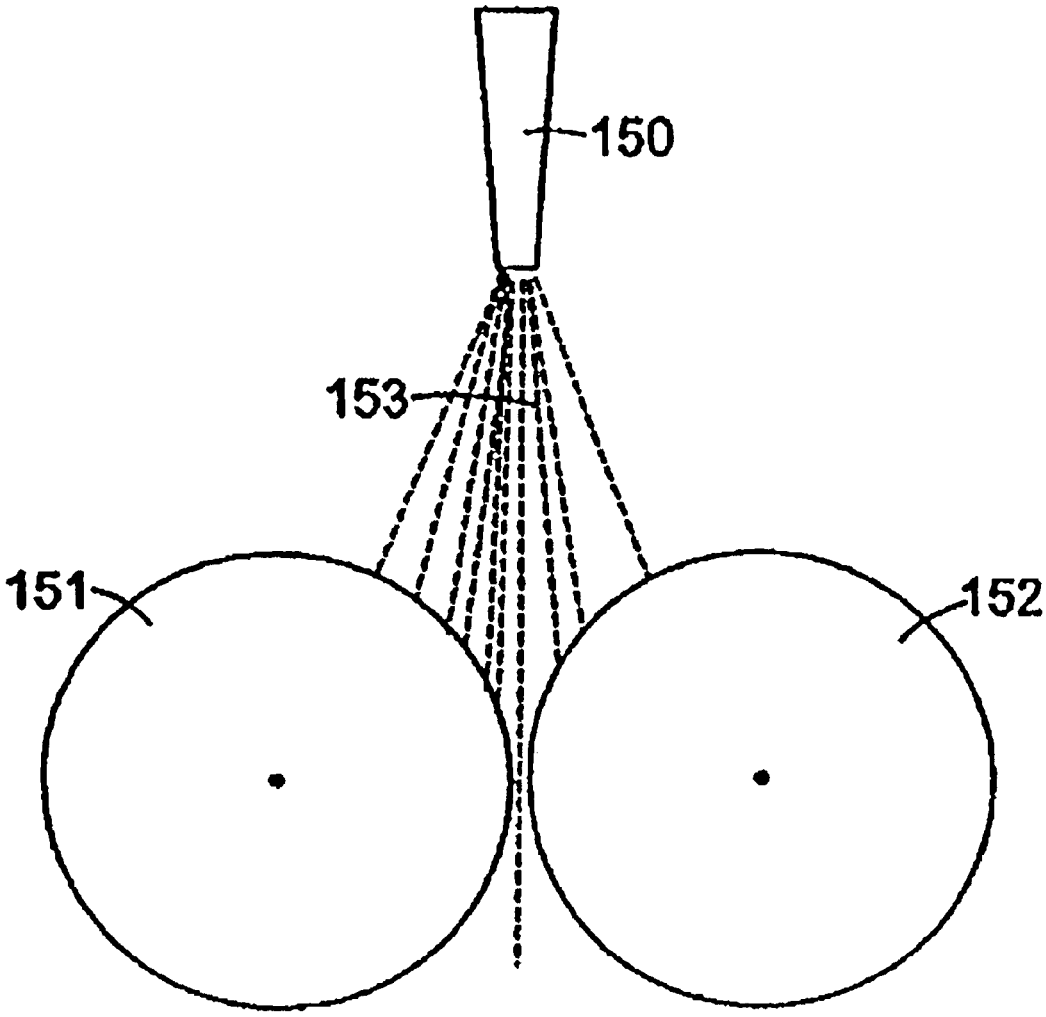
FIG. 18 is an illustration of a comparative example showing a spray nozzle having a spray pattern and a pair of rollers.

FIG. 18 is an illustration of a comparative example. As illustrated in FIG. 18, spray nozzle 150 produces spray pattern 153 wherein the majority of the spray from spray pattern 153 is deposited on the first 151 and second 152 rollers (no rollable device shown). This kind of spray pattern can ultimately lead to coating defects. Coating defects include uneven application of the coating material on the surface of the device and unintended variations in the amount of material applied to the device.

Spray Nozzle

According to the invention, the spray nozzle can be any sort of droplet producing system that either A) produces a spray of a coating material that is directed towards the gap between the rollers where a majority of the sprayed coating material passes through the gap, or B) that is configured to produce a spray of coating material having a spray pattern wherein the width of the spray pattern at the gap that is not greater than 150% of the width of the gap. Typically, the spray nozzle is configured to produce a spray having a narrow spray pattern.

The spray nozzle of the coating apparatus can be a jet nozzle. Suitable jet nozzles, for example, jet nozzles found in ink jet printers, can be obtained from The Lee Company (Westbrook, Conn.). Various types of ink jet nozzles are contemplated, for example, thermal inkjet nozzles which utilize thermal energy to emit solution from the nozzle via a pressure wave caused by the thermal expansion of the solution; electrostatic inkjet nozzles wherein a solution is emitted from the nozzle by electrostatic force; piezoelectric inkjet nozzles in which solution is ejected by means of an oscillator such as a piezoelectric element; and combinations of these types of inkjet nozzles.

Figure 11:
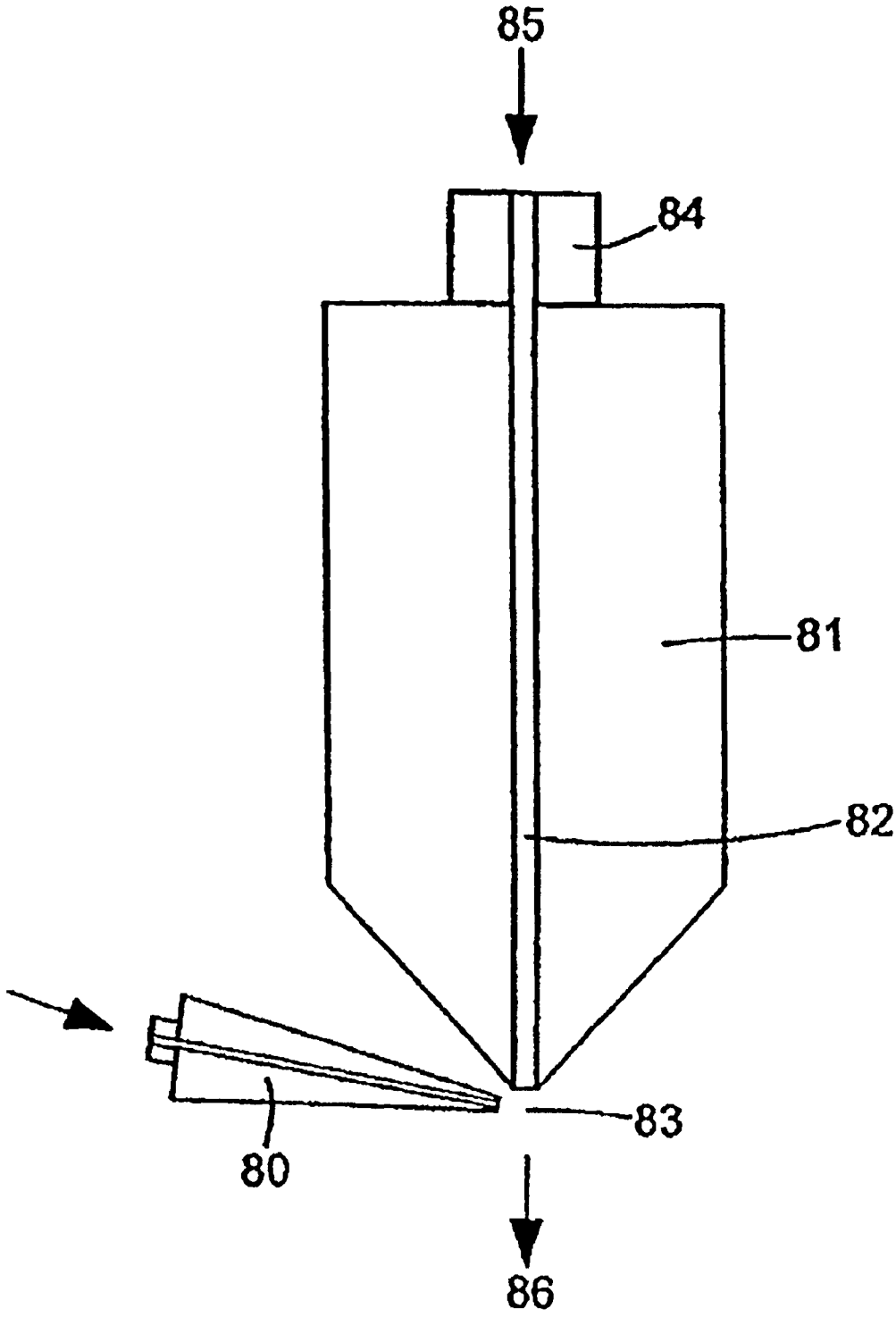
FIG. 11 is an illustration of a sonicating nozzle.

In a preferred embodiment of the invention, the spray nozzle is a sonicating nozzle. A preferred arrangement of a sonicating nozzle is illustrated in FIG. 11, the sonicating nozzle can have at least two independent members: a solution delivery member 80 and an air delivery/sonicating member 81. The air delivery/sonicating member 81 includes a channel 82 bored through the body of the air delivery/sonicating member 81. Gas can be provided from a gas delivery line (not shown) to an inlet 84 on the air delivery/sonicating member 81 and can travel through the channel 82 to the tip 83 where a stream of gas is generated. A coating solution is delivered through solution delivery member 80 via a solution delivery line (not shown) to the tip 83 of the nozzle, where, at this point, the solution is sonicated at the tip 83 of the air delivery/sonicating member 81, producing droplets of solution, and the droplets are drawn into and carried by the gas stream originating at the tip 83 of the nozzle.

Various nozzles can produce spray patterns having different shapes. FIG. 12 illustrates a spray pattern that can be generated from a sonicating nozzle. The sonicating nozzle 5 can produce a spray pattern 90 having a focal point at a distance from the tip 5 of the nozzle 71. The spray pattern produced by this type of ultrasonicating nozzle is considerably narrower than many other spray patterns generated from traditional types of spray nozzles. A suitable sonicating nozzles is the MICROFLUX XL nozzle sold by Sono Tek (Milton, N.Y.). This spray nozzle is able to provide a spray pattern having a minimal width of 0.030 inches (0.768 mm). Nozzles producing other spray patterns, such as patterns having a conical shape (not shown) and that fall within the context of the invention are also contemplated.

Delivery of the coating material in the form of a spray can be affected by various operational aspects of the sonicating nozzle. These include the rate of delivery of the solution, the size of the orifice of the solution delivery member, the distance of the solution delivery member from the tip of the sonicator/air delivery member, the tip size and configuration of the sonicator, the amount of energy provided to the sonicator, the size of the orifice at the outlet of the gas channel, the rate of delivery of gas from the gas delivery port (air pressure), and the type of gas delivered from the nozzle.

Referring back to FIG. 4, the tray 3 having one or more pairs of rollers 4 can be situated in a coating zone 6 on the top of the housing 2 of the apparatus 1. The coating zone 6 is an area on the housing 2 where the spray coating process takes place and the area in which spray nozzle 5 is movable. The spray nozzle 5 is movable via first track 7 and second track 8, which will be discussed in greater detail below.

Tray 3 can be positioned in the coating zone 6 by actuation of an alignment system (not shown). Actuation of the alignment system can allow the precise placement of the pair of rollers under the spray nozzle 5, wherein the gap 70 between the first and second rollers is precisely aligned with the tip 71 of the spray nozzle 5. The alignment system of the current invention can include, for example, insertable and retractable alignment pins (not shown) that protrude from the housing 2. The tray 3 having one or more roller pairs 4 can include positioning holes (not shown) that accept the alignment pins. The tray 3 can be moved into the coating zone either manually or automatically and the alignment system can be actuated to insert the alignment pints into the positioning holes thereby aligning the tip 71 of the spray nozzle 5 with gap 70.

In another embodiment, referring to FIG. 5, tray 21 having a pair of rollers 4 can be brought into the coating zone via track 22 which can be a part of a conveyor mechanism.

Figure 6:
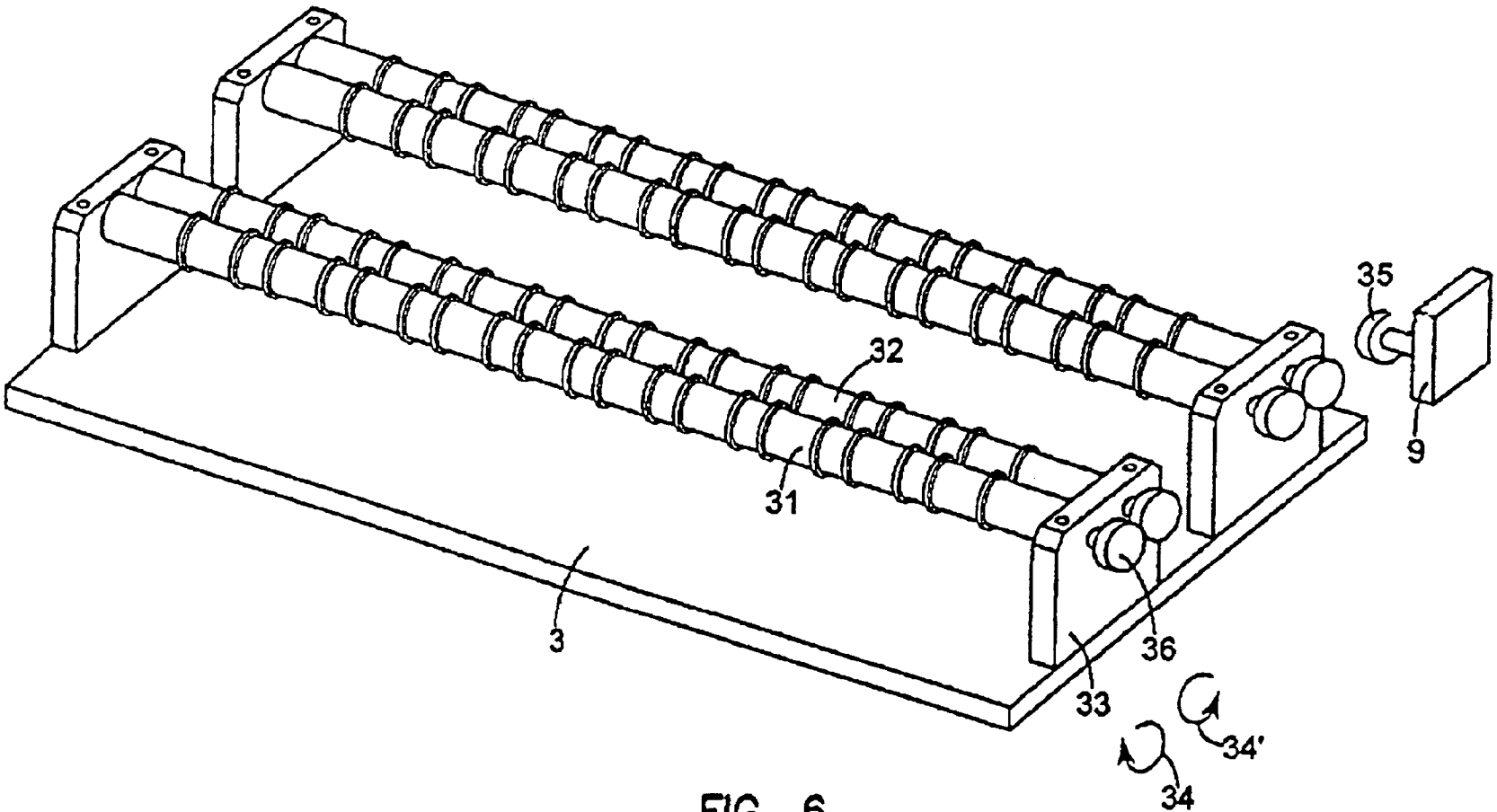
FIG. 6 is an illustration of two pairs of rollers attached to a tray.

When the pair of rollers 4 are properly situated in the coating zone, a portion of the rollers can engage a roller drive mechanism that can cause rotation of the rollers. Referring to FIG. 4, tray 3 having at least one pair of rollers 4 is positioned in a coating zone 6 and at least a portion of one pair of rollers is brought into contact with a roller drive mechanism 9. Referring to FIG. 6, either distal end of the first roller 31 or the second roller 32 is configured to engage a shaft 35 of the roller drive mechanism 9. The distal portion of the roller that engages the shaft 35 of the roller drive mechanism 9 can include a meshing/engagement member 36, such as a sprocket, gear, or a rounded member. Either or both the distal portions of the first roller 31 and the second roller 32 can include a meshing/engagement member 36. Rotation of the shaft 35 by actuating the roller drive mechanism 9 causes rotation of first roller 31, the second roller 32, or both the first and second roller. Typically, both the first roller 31 and second roller 32 are rotated by the roller drive mechanism 9 in a direction as indicated by arrow 34 or in a direction as indicated by arrow 34'.

In another embodiment, the distal portion of first roller 31, the second roller 32, or both the first and second roller can be connected to a continuous drive member (not shown) such as a belt or chain. One or both rollers from more than one pair of rollers 4 can be connected to the continuous drive member. When a tray including more than one pair of rollers 4, each pair of rollers connected to a continuous drive member, is positioned in the coating area, the shaft 35 of the roller drive mechanism 9 can engage the meshing/engagement member 36 of the roller and cause rotation of all of the rollers on the tray via the continuous drive member.

The roller drive mechanism 9 can also have an indexing function which allows for intermittent rotation of the shaft 36 which translates to intermittent rotation of the rollers. The indexing function of the roller drive mechanism 9 can allow rotation of the rollers in a manner sufficient to rotate devices that are situated on the rollers. The indexing function of the roller drive mechanism 9 will be described in greater detail below.

According to the invention, the coating apparatus can include a spray nozzle 5 that is movable in a direction that is parallel central axis of the roller or is both parallel and perpendicular to the central axis of the roller.

In one embodiment, referring to FIG. 4, the spray nozzle 5 can be moved in directions according to arrows 10 and 10', which is parallel to the central axis of the rollers 4, and arrows 11 and 11', which is perpendicular to the central axis of the rollers 4. As illustrated in FIG. 4, spray nozzle 5 is attached to nozzle mount 12 which is attached to and movable in directions 10 and 10' on first track 7 of movable arm 13. Movable arm 13 is attached to second track 8 which is included in panel 14 and movable in directions 11 and 11'. Nozzle mount 12 can be moved on the first track 7 by the operation of a first track drive (not shown). A first track motor (not shown) can drive the movement of the first track drive, which can be a belt, chain, pulley, cord, or gear arrangement; operation of the first track motor allows the nozzle mount 12 to travel in directions 10 and 10'. Movable arm 13 is connected to second track 8 and movable in directions 11 and 11'.

In another embodiment, as illustrated in FIG. 5, the spray nozzle 5 is movable in either direction according to arrows 10 and 10' and at least one pair of rollers 4 are movable in directions 23 and 23' either manually or automatically. One pair of rollers is typically attached to a single tray 21. The spray nozzle can travel in either direction 10 or 10' during the process of disposing a coating material on a substrate. After spray nozzle 5 has completed a coating process, the tray 21 can be moved from the coating zone and another tray can enter the coating zone.

Methods of Coating a Rollable Device

The coating apparatus and methods described herein provide numerous advantages for coating rollable devices. In particular, the apparatus is very suitable for coating small objects, such as small medical devices having a cylindrical or tubular shape.

Generally, the method of using the coating apparatus includes coating a rollable device by first placing a rollable device on a device rotator which includes a pair of rollers having a gap. The rollable device is generally supported by the pair of rollers and is positioned between the gap and a tip of a spray nozzle. In one embodiment, both the width of the gap and the width of the spray pattern are less than the size of the device (i.e., the diameter of the device). A coating material is then disposed from a spray nozzle and at least a portion of the coating material becomes deposited on the device. Typically, the portion of the device that is most proximal to the tip of the spray nozzle receives a coating. The coating material that is applied to the device is produced from the spray nozzle in a spray pattern that is directed at the gap. The majority of any spray that does not get deposited on the device passes through the gap. For example, devices such as stents typically have openings in their structure that can allow the sprayed coating material to pass through. After the coating material is applied to the device, the device can be rotated according to the movement of the first or second roller and the step of disposing a coating material can be repeated a desired number of times.

According to the invention, any device that is suitable for receiving a coating material and being rotated utilizing the apparatus described herein can be used as a device in the coating process. Generally, the device has shape that can allow the device rotator to rotate the device during the coating process. The device can have, for example, a circular shape or a polygonal shape.

The coating apparatus is particularly useful for coating devices having a tubular or cylindrical shape such as catheters and stents. In one embodiment the method includes coating rollable devices that have holes in their structure, such a stents, or other rollable devices that include webbed-like structures, or that have spaces, apertures, openings, or voids. These devices can be coated but typically allow the passage of a sprayed material through the device. The coating apparatus is particularly suitable for coating rollable devices having a diameter of 5 cm or less and more particularly for devices having a diameter that is 10 mm or less.

Medical devices which are permanently implanted in the body for long-term use (i.e., long term devices) or used temporarily (i.e., short term devices) in the body are contemplated. Long-term devices include, but are not limited to, grafts, stents, stent/graft combinations, valves, heart assist rollable devices, shunts, and anastomoses devices; catheters, such as central venous access catheters; and orthopedic devices, such as joint implants. Short-term devices include, but are not limited to, vascular devices such as distal protection devices; catheters such as acute and chronic hemodialysis catheters, cooling/heating catheters, and percutaneous transluminal coronary angioplasty (PTCA) catheters; and glaucoma drain shunts.

In order to apply a coating material to the rollable device, the rollable device is first placed on the pair of rollers 4, making contact with the first roller 31 and second roller 32. The device can be placed on the rollers manually, or, in some embodiments, can be placed on the rollers automatically, for example, using a robotics system. Typically, multiple devices are placed on the pair of rollers 4 along the length of the rollers. The number of devices placed on the pair of rollers 4 may depend on the size of the device and the length of the pair of rollers 4.

In another embodiment, a plurality of devices can be placed on multiple pairs of rollers, the multiple pairs of rollers attached to a single tray (for example, referring to the tray of FIG. 6). A tray having more than one pair of rollers can accommodate a plurality of devices.

In some embodiments, the devices are placed along a pair of rollers, the rollers having a plurality of ribs 41 (for example, referring to the roller in FIG. 7). An individual device is typically contacted by at least three ribs 41 from a pair of rollers having ribs to ensure rotation of the device when the rollers are rotated.

Prior to the spraying of a coating material from the spray nozzle 5, devices placed on a pair of rollers 4 are brought into a coating zone. The coating zone is an area on the housing 2 generally where the spray coating process takes place and is generally the area in which spray nozzle 5 is movable.

In one embodiment and referring to FIG. 4, the coating zone includes the area in which tray 3 is located. Spray nozzle 5 is movable to any position over tray 3. More specifically, spray nozzle 5 is movable along the central axis of the pair of rollers 4 in directions 10 and 10' and also in a direction perpendicular to the plane of the first and second axis, in directions 11 and 11'. Tray 3, having multiple pairs of rollers 4, can be brought into the coating zone 6 and aligned via an alignment system. Tray 3 can be moved into the coating zone manually or automatically and the alignment system can be actuated to insert alignment pairs into the positioning holes, thereby aligning the tip 51 of spray nozzle 5 with the gap 71 between the first roller 31 and the second roller 32.

When the tray is positioned in the coating zone it can also brought into contact with roller drive mechanism 9. Shaft 35 of the roller drive mechanism 9 can engage the distal portion of one roller of the roller pair 4 via a meshing/engagement member 36. Rotation of the shaft 35 by actuating the roller drive mechanism 9 causes rotation of first roller 31, the second roller 32, or both the first and second roller. The distal portion of first roller 31, the second roller 32, or both the first and second roller can also be connected to a continuous drive member (not shown) such as a belt or chain. One or both rollers from more than one pair of rollers can be connected to the continuous drive member. When the tray 3 including at least one pair of rollers 4 is positioned in the coating area, the shaft 35 of the roller drive mechanism 9 can engage the continuous drive member. Actuation of the roller drive mechanism 9 can cause rotation of the one or both rollers of one or more roller pairs.

During the step of disposing a coating material on the rollable device, a coating solution is dispensed from the spray nozzle and directed at the rollable device towards the gap between the first and second roller. In some coating procedures the device can be a device having few or no pores in its structure. In other coating applications the device can be a device having considerable porosity or openings in its structure. In coating devices that have considerable porosity or openings, a portion of the coating material will be directed through these openings. According to the invention, the majority of the coating material that is not deposited on the surface of the device passes through the gap. In this arrangement, significant accumulation of coating material on the rollers is avoided. This is advantageous in many regards. For example, it avoids pooling of the coating material at the points where the device contacts the first and second rollers. In addition, it reduces the amount of coating material wasted during the coating process, resulting in a more cost-effecting approach to coating.

During the coating process either a portion or the entire rollable device can be coated. Typically, the entire periphery of the device, at least, is coated during the coating process. This can be achieved by repeatedly applying coating material and rotating the device between the applications of coating material. During one application generally not more than one half of the device is coated with the coating material. More typically, not more than one quarter of the device is coated and even more typically not more than one eighth of the device is coated during a coating application. Generally, about 10 applications of the coating material are generally required to completely coat the circumference of the device. When small medical devices such as stents are coated it is typical to apply at least 10 applications of the coating material to provide a useful amount of coating material to the device surface. In other processes it may be desirable only to coat a portion of the device.

In one embodiment the coating material is applied from a sonicating nozzle. Referring to FIG. 11, the sonicating nozzle can include a solution delivery member 80 and an air delivery/sonicating member 81. A suitable sonicating nozzle is the MicroFlux XL nozzle sold by Sono Tek (Milton, N.Y.). In some embodiments, in the step of disposing the coating material from the sonicating nozzle, air is supplied to the nozzle in the range of 0.5–5 psi and more specifically in the range of 2–3 psi. The coating solution is supplied to the nozzle in the range of 0.1–0.4 ml/min, and the power of the sonicating tip can be in the range of 0.1–2 watts. Although the distance from the tip of the nozzle to the most proximal portion of the device can be variable, a preferred range is 1–10 mm and more preferably 2–4 mm. The width of the applied coating material can be variable although typical widths are in the range of 0.75 mm to 10 mm on the surface of the device.

The step of disposing a coating material on the device can be performed at any temperature suitable for producing a spray according to the compounds and solvents used. The coating temperature can also be adjusted to promote or prevent, for example, drying of the coating material on the device. In some embodiments coating of the device is performed in a regulated atmosphere, for example, in an atmosphere having a reduced water vapor content (i.e., reduced humidity).

While the coating is disposed from the nozzle onto the rollable device, the spray nozzle can be simultaneously moved in a direction parallel to the axis of the rollers (i.e., in direction 10 or 10'), providing a spray coating for devices that are positioned on the pair of rollers. The spray nozzle 5 can be attached to an arm 12 which is movable in a direction along the axis of the pair of rollers 4 (i.e., in direction 10 or 10') on track 7. Movement of the spray nozzle 5 along the axis while applying a coating to the device results in a "stripe" of coating material on the devices. Stripes of coating material can be applied to a plurality of devices that are positioned along the length of the pair of rollers 4. According to the invention, at least the majority of the coating material that does not get deposited on the device passes through the gap 71 between the first and second rollers. Therefore the rollers do not accumulate any significant amount of coating material during the spray application.

The devices can then be rotated on the pair of rollers, for example, by using an indexing function, to position an uncoated portion of the device in line for an application of sprayed coating material. In one embodiment, the device is rotated by indexing the rollers which can proceed in a clockwise or counter clockwise pattern. In a preferred embodiment the devices are randomly indexed between applications of the coating material. For example, random indexing can proceed in both clockwise and counterclockwise directions. The devices can be indexed multiple times during a coating process, for example, between 10–200 times. Following rotation of the devices by the indexing function, another step of disposing the coating material can then be performed. The steps of applying a coating material and rotating the device can be repeated until the device is sufficiently coated, for example, until the device is coated with a certain amount of coating material.

Operation of the entire coating apparatus can be controlled automatically or portions of the coating apparatus can be controlled manually. For example, the coating apparatus can include a central comuterized unit that can be programmed to perform an entire coating process. The central computerized unit can control functional aspects of the coating apparatus, for example, the dispense rate of the coating solution; the energy and air pressure supplied to the sonicating spray nozzle; the movement, rate of movement, and positioning of the spray nozzle (as driven by the track motors and track drives); the alignment of the tray on the housing; and the rotation of the rollers by the roller drive mechanism. It is understood that coating parameters can be established and programmed into the central computerized unit that allow a particular amount of coating material to be deposited on a device during a coating procedure.

According to the method of the invention, the steps of coating and rotating the device can allow for the coating process to be performed before the coating material dries on the device. Typically, in ambient conditions, the majority of drying is not achieved until 30 minutes after coating and more typically not until one hour after coating. Drying can still occur after these times, for example, up to 24 hours after application of the coating material. Traditional procedures have required that the coated device dries at least 30 minutes before it is manipulated.

However, according to the apparatus and the methods of this invention, it has been discovered that the device can be rotated, placing the coated portion of the device in contact with the rollers, prior to any significant drying of the deposited coated material. For example, the device can be coated and, within seconds, rotated, placing the coated portion of the device in contact with the rollers without compromising the integrity or quality of the coated portion. In the coating process described herein, the device is typically rotated approximately 5–15 seconds after a coating is applied to a portion of the device. However, longer or shorter times between coating the device and rotating the device are contemplated as it is not necessary that the coating material dries prior to rotation. Allowing the coating material to dry prior to contacting either the first or second roller is optional. The process of coating, rotating, and repeating the coating steps dramatically reduces the processing time standardly associated with spray coating a device such as a small medical rollable devices. In addition, there is no requirement that the devices be fixtured (i.e., held by a clamping mechanism) during the coating process. Avoiding fixturing reduces the possibility of introducing defects in the coating applied to the device. The coating method described herein produces coatings demonstrating a low degree (less than 5%) of variability in the amount of coating applied from one coated device to another coated device.

Following the steps of disposing a coating material on the device and rotating the device, the coated devices can be removed from the roller pairs and dried or can be allowed to dry on the roller pairs. Alternatively, the rollable devices can be allowed to dry on the rollers.

In an embodiment, the invention can be used for batch process coating of a plurality of devices. By way of example, embodiments can be used to coat a plurality of devices in a consistent manner all as a part of a batch.

In an embodiment, the invention includes a bi-directional indexing movement. Specifically, in an embodiment, the invention includes an indexing step wherein the rollers are first turned backward to release any sticking between the lead roller and the device to be coated before being turned forward to rotate the device to be coated so that a different portion of it is covered by the coating solution. When referring to individual rollers of a pair of rollers, when both rollers rotate in the same direction, one roller can be referred to as a lead roller and one roller can be referred to as a trailing roller. The lead roller is the one that has a surface that rotates up and away from the gap between the rollers, while the trailing roller is the one that has a surface that rotates down and into the gap between the rollers. In some circumstances, such as when the invention includes a bi-directional indexing movement, the rollers can sometimes turn in one direction and other times turn in the opposite direction. In embodiments including a bi-directional indexing movement, the rollers may rotate a greater amount in one of the directions. That is, in order to advance the device so that a different surface is exposed to the spray nozzle, rotation in one direction (the predominant direction) must be greater than rotation in the opposite direction. In these circumstances, the lead roller is the roller that has a surface that rotates up and away from the gap between the rollers when the rollers are rotating in the predominant direction.

Referring now to FIG. 19, a schematic cross-sectional view of a coating system is shown that has a bi-directional indexing movement. Lead roller 801 and trailing roller 802 are disposed with a gap 804 between the rollers. A rollable device 803 is disposed between the rollers in the gap 804. When it is time for the coating system 800 to index the rollable device 803 into the next coating position, the lead roller 801 and the trailing roller 802 first rotate in the direction of arrows 811 to release any sticking that may have occurred between the rollable device 803 and the lead roller. At this stage, it is possible that the rollable device 803 may stick to the trailing roller 802. However, the rollers next turn in the direction of arrows 812 such that the rollable device 803 will move back into the gap 804, if out of position, and be pressed against the lead roller 801 in order to release any adhesion between the rollable device 803 and the trailing roller 802. Thus, in an embodiment, the second rotation movement of the rollers is in the opposite direction of the first rotation movement. In an embodiment, the second rotation movement rotates the rollable device 803 farther than the first rotation movement. In this manner, the surface 816 of the rollable device that faces the spray stream is different that the surface that was facing the spray stream before the two rotation movements took place. In an embodiment, the invention includes bi-directional rotation member. The bi-directional rotation member can be operably attached to a pair of rollers and configured to provide the rollers with a bi-directional indexing movement.

Apparatus for Reducing Sticking or Static Adhesion

In an embodiment, the invention includes a spray system wherein the spray stream is biased toward the trailing roller. Referring to FIG. 20, an air delivery/sonicating member 307 is shown in association with a solution delivery member 311. In this figure, rollers 301, 302 are shown to rotate in the direction of arrows 305 (counter-clockwise). In this case, roller 301 is the lead roller since the rotational path of its surface is up and away from the gap 304 between the two rollers. Although in many embodiments rotation of the rollers and deposition of coating solution would not occur simultaneously, they are shown together in FIG. 20 for purposes of illustration. A stream of nitrogen passes through a channel 309 in the air delivery/sonicating member 307. Coating solution is delivered through a channel 313 in the solution delivery member 311. The coating solution contacts the air delivery/sonicating member 307 before being dispersed and is then pushed downward to form a spray stream 315 by the flow of nitrogen coming out of the air delivery/sonicating member 307. In this embodiment, the air delivery/sonicating member 307 is shifted in the direction of arrow 317 (toward the trailing roller) from a point that would be directly above the gap 304 in between the rollers. This causes the spray stream 315 to be biased toward the trailing roller 302. In an embodiment, the spray stream 315 can also be biased toward the trailing roller by orienting the air delivery/sonicating member 307 to point toward the trailing roller.

Because the spray stream 315 is biased toward the trailing roller 302, an amount of coating solution may be deposited on the trailing roller 302. While some coating solution may also get deposited on the leading roller 301, it will generally be a lesser amount than that amount deposited on the trailing roller 302. While not intending to be bound by theory, since it is believed that sticking is influenced by coating solution being deposited on the rollers, having less coating solution deposited on the leading roller 301 can result in less sticking to the leading roller 301. With the spray stream biased toward the trailing roller 302, sticking to the trailing roller 302 could occur. However, sticking to the trailing roller 302 is less problematic to the coating process because the sticking can be released when the rollable device is pushed down into the gap 304 between the rollers.

In an embodiment, the invention includes a repositioning member that is disposed on the coating apparatus. As discussed above and illustrated in FIG. 2, rollable device 203 can stick to the lead roller 202 at point 206 and move in the direction of arrow 209 on the surface of lead roller 202, as lead roller 202 turns clockwise. This means the rollable device 203 may no longer occupy the gap area 204 between the rollers where the spray of a coating solution will be directed. Referring now to FIG. 21, a coating device 400 is shown having a lead roller 401 and a trailing roller 402 that both generally turn in the direction of arrow 405. A rollable device 407 is positioned in the gap area 404 that lies between the two rollers. A repositioning member 411 is positioned a distance 413 from the surface 415 of the lead roller 401 that is slightly less than the distance which corresponds to the diameter 409 of the rollable device 407.

Referring now to FIG. 22, a coating device 400 is shown wherein the rollable device 407 has stuck to the lead roller 401 and moved out of the gap area 404 between the rollers. However, the rollable device 407 contacts the repositioning member 411 that is positioned a distance 413 from the surface 415 of the lead roller 401. When the rollable device 407 contacts the repositioning member, sticking is released and the rollable device 407 rolls back down into the gap area 404.

Figure 24:
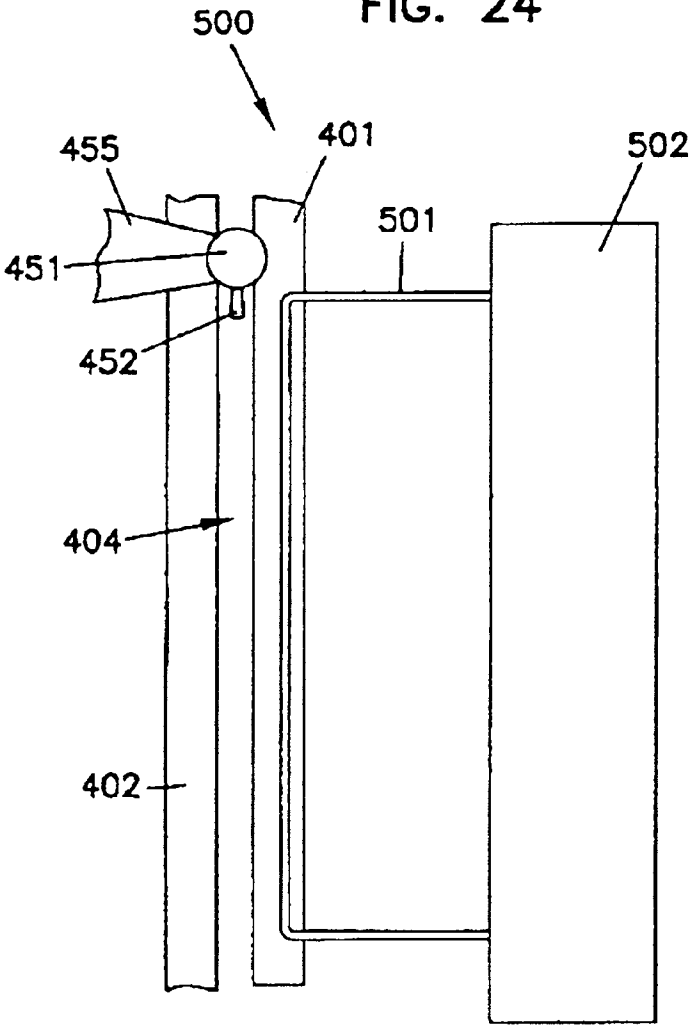
FIG. 24 is a schematic top view of a coating apparatus in accordance with an embodiment of the invention having a device retaining member.
Figure 23:
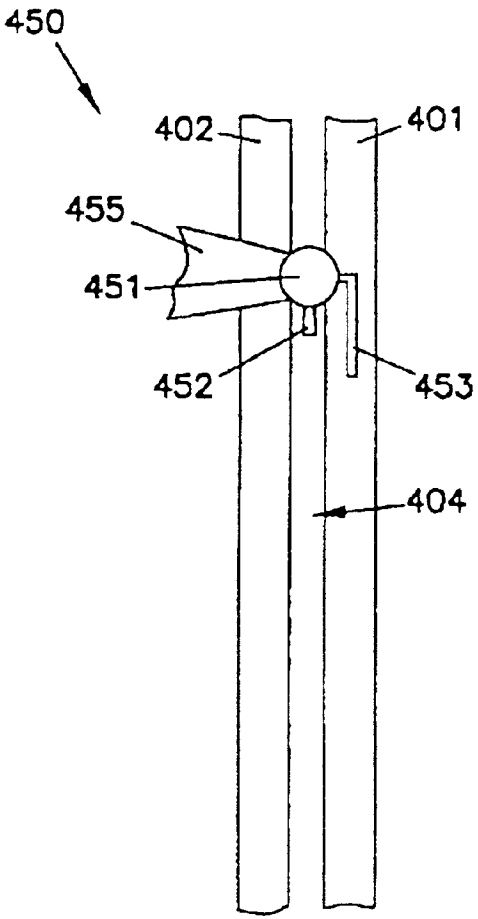
FIG. 23 is a schematic top view of a coating apparatus in accordance with an embodiment of the invention having a device retaining member.

The repositioning member can be shaped in various ways and disposed on various elements of the coating system. For example, FIG. 23 shows one embodiment of a repositioning member 411 as repositioning bar 453. In this embodiment, there is a lead roller 401 and a trailing roller 402. Further, there is a gap 404 in between the rollers. There is an air delivery/sonicating member 451 and a solution delivery member 452. In this embodiment, the repositioning bar 453 is attached to the spray head support structure 455. In FIG. 24, a different embodiment is shown. In this embodiment, there is a lead roller 401 and a trailing roller 402. Again, there is a gap 404 in between the rollers. There is also an air delivery/sonicating member 451 and a solution delivery member 452. In this embodiment, the repositioning member 501 is shown attached to a separate repositioning member support structure 502.

Figure 25:
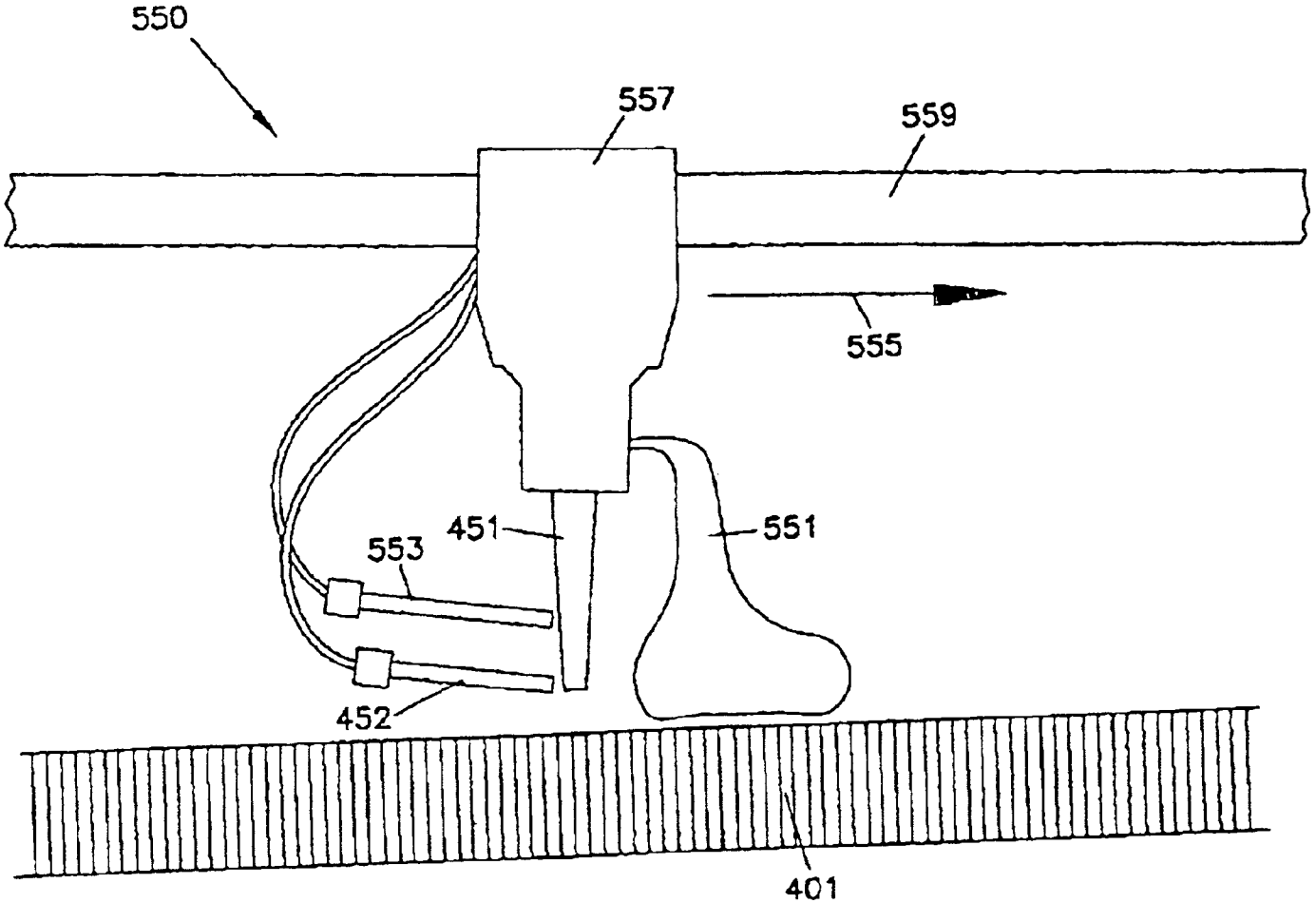
FIG. 25 is a side view of a coating apparatus in accordance with an embodiment of the invention having a repositioning member.

Referring now to FIG. 25, a side view of a coating apparatus 550 in accordance with an embodiment of the invention having a repositioning member is shown. A movement support structure 557 is operably attached to a rail 559. The movement support structure 557 can move along the rail 559. Air delivery/sonicating member 451 is attached to the movement support structure 557. Solution delivery member 452 is configured to provide a coating solution to the air delivery/sonicating member 451. In this view, a wash solution delivery member 553 is configured to provide a wash solution onto the air delivery/sonicating member 451 periodically when cleaning is required. A repositioning loop 551 is attached to the movement support structure 557. The repositioning loop 551 is positioned so that as the movement support structure moves in the direction of arrow 555, the repositioning loop 551 is in a position to contact any rollable devices that may have moved out of the proper coating position and onto lead roller 401. The repositioning loop 551 may be made of a variety of materials including a polymer, metal, cellulose, a composite, and the like. In the embodiment shown in FIG. 25, the repositioning member only extends in the direction of arrow 555. However, in other embodiments, the repositioning member also extends in the direction opposite of arrow 555. In this manner, the repositioning loop 551 can be in a position to contact any rollable devices that may have moved out of the proper coating position and onto lead roller 401, before the air delivery/sonicating member 451 passes over the errant rollable device, whether movement support structure 557 is moving in the direction of arrow 555 or in the opposite direction. In an embodiment, there are two repositioning members, one extending in the direction of arrow 555 and one extending in the opposite direction.

In an embodiment, the invention includes a structure for blowing a stream of a gas that pushes rollable devices back into the proper position. Referring to FIG. 26, a lead roller 401 and a trailing roller 402 are shown that turn in the direction of arrow 405. A gap 404 is between the rollers. A rollable device 407 has stuck to the lead roller 401 and moved out of the gap 404 as the lead roller has rotated in the direction of arrow 405. A gas supply structure 602 has a channel 604 through which a stream of gas 606 blows out that intersects rollable device 407 when it is lifted out of the gap 404 between the rollers. The stream of gas 606 contacts the rollable device and helps to reposition the rollable device back into the gap 404. If too strong of a stream of gas is provided, it may push the rollable device off of the apparatus or cause damage to the rollable device. If too weak of a stream of gas is provided, it will not help to reposition the rollable device back into the gap 404. In an embodiment, stream of gas is provided in an amount effective to push rollable medical devices into the gap. One of skill in the art will appreciate that the stream of gas may comprise any suitable gas. In an embodiment, the stream of gas comprises pure nitrogen.

Figure 27:
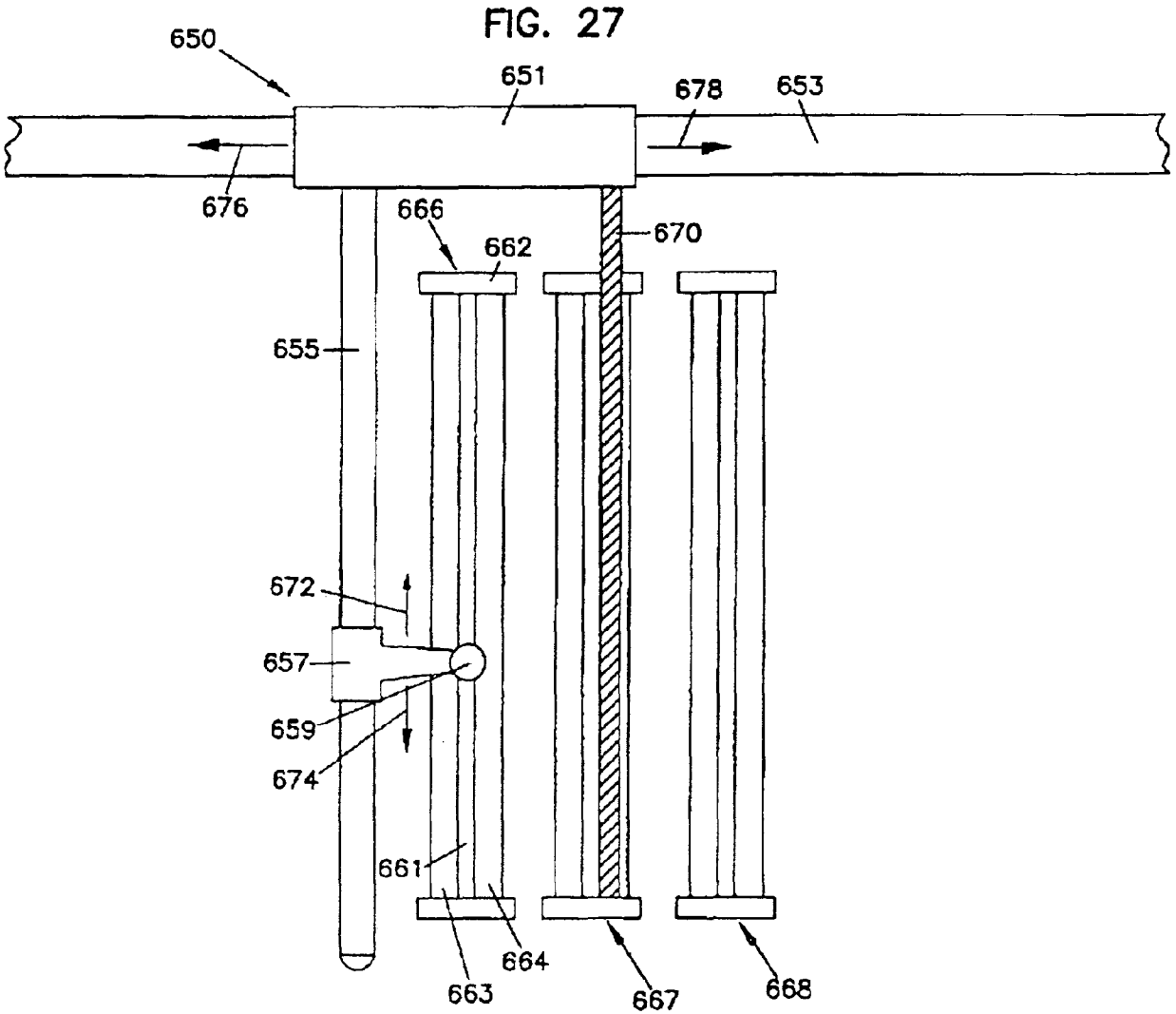
FIG. 27 is a top view of a coating apparatus in accordance with an embodiment of the invention having an air knife.

Referring now to FIG. 27, a top view of a coating apparatus in accordance with an embodiment of the invention having a gas repositioning structure, or air knife, is shown. An air delivery/sonicating member 559 is attached to a lateral movement support structure 657. Lateral movement support structure 657 is operably attached to a lateral rail 655. Lateral movement support structure 657 can move along lateral rail 655 in the directions of arrows 672 and 674. Lateral rail 655 is attached to longitudinal movement support structure 651. Longitudinal movement support structure 651 is operably attached to longitudinal rail 653. Longitudinal movement support structure 651 can move along longitudinal rail 653 in the directions of arrows 676 and 678. In this example, the air delivery/sonicating member 559 is positioned so that a coating material can be applied to rollable devices (not shown) disposed in the gap 661 in a roller assembly 666. Air knife 670 is operably attached to longitudinal movement support structure and is arranged over a different roller assembly 667. However, in an embodiment, the air knife 670 can be operably attached to the longitudinal movement support structure and arranged over the same roller assembly 666 as the air delivery/sonicating member 559. A gas can be expelled from the underside of air knife 670 that can act to push down any rollable devices that have gotten out of proper coating position. After the air delivery/sonicating member 559 has applied coating material to the rollable devices (not shown) disposed in the gap 661 in roller assembly 666, the longitudinal movement support structure 651 moves along longitudinal rail 653 in the direction of arrow 678 so that air delivery/sonicating member 559 will be in position to apply coating material to rollable devices help by roller assembly 667. Because, air knife 670 is also attached to longitudinal movement support structure 651, air knife 670 is now positioned to expel a gas onto any rollable devices that have gotten out of proper coating position on roller assembly 668. In this manner, the air knife 670 precedes the air delivery/sonicating member 559 so that any rollable devices that have gotten out of proper coating position are repositioned before the air delivery/sonicating member 559 applies coating material to them.

Figure 28:
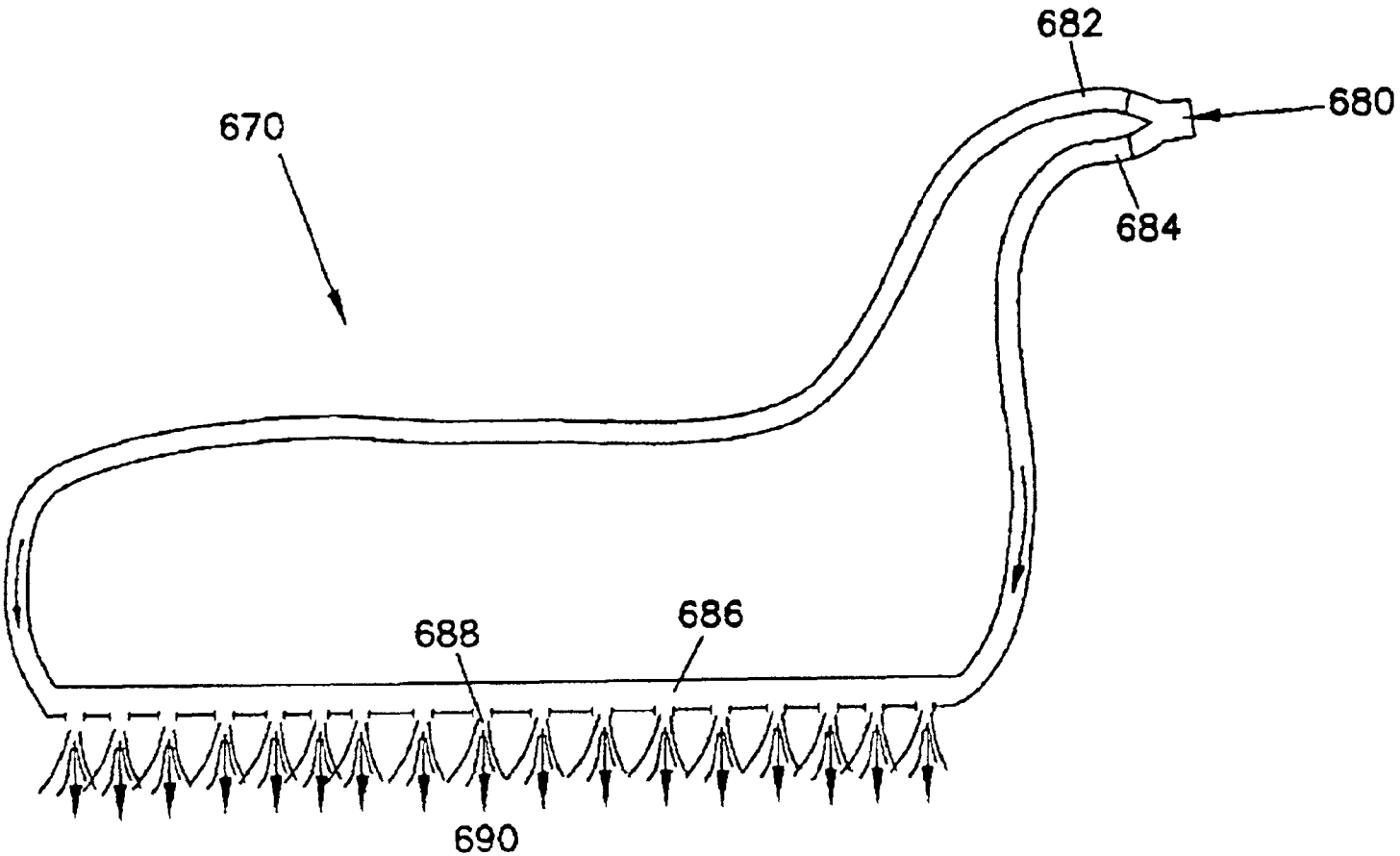
FIG. 28 is a cross-sectional side view of an air knife in accordance with an embodiment of the invention.

Referring now to FIG. 28, a cross-sectional side view of an air knife 670 in accordance with an embodiment of the invention is shown. A gas supply is connected to a gas supply port 680 which is connected to two gas delivery channels 682, 684. Gas delivery channels 682, 684, meet at a lateral gas application member 686. A plurality of apertures, such as aperture 688, are defined by the underside of the lateral gas application member 686. Gas pressure inside of later gas application member 686 forces gas out of the plurality of apertures, such as aperture 688, and in the direction of arrow 690. One of skill in the art will appreciate that air knife 670 can be configured in many different ways while still being able to direct gas in the direction of arrow 690.

It has been surprisingly discovered that the spray pattern coming off of a sonicating nozzle can produce more overspray in the opposite direction of the solution delivery member. For example, referring now to FIG. 29, a coating system 700 is shown. In this system, there is a lead roller 701 and a trailing roller 702. Both the lead roller 701 and the trailing roller 702 rotate in the direction of arrows 703. There is a conduit 706 that passes through the air delivery/sonicating member 705, through which a stream of nitrogen or another gas can travel. A solution delivery member 708 has a channel 710 through which a coating solution can pass before a spray stream 712 of solution is generated. The stream of nitrogen that passes through air delivery/sonicating member 705 pushes the spray stream toward the gap 704. An amount of overspray 714 tails off spray stream 712 on the opposite side of the air delivery/sonicating member 705 from the solution delivery member 708. This amount of overspray 714 can be deposited on one of the rollers. In this case, it is deposited on the lead roller 701 which can lead to sticking problems with a rollable device.

Figure 30:
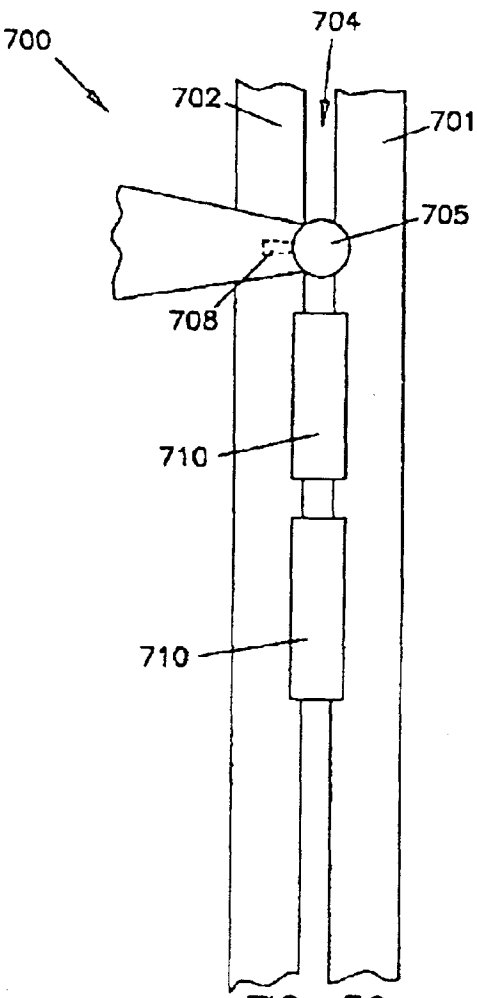
FIG. 30 is a schematic top view of the coating apparatus of FIG. 25.

In FIG. 30, a top view of the coating apparatus 700 of FIG. 25 is shown. In this view it can be seen that the solution delivery member 708 (in phantom lines) is disposed perpendicular to the main axis of the rollers 701, 702. As previously described, in this configuration, amounts of overspray are present in the opposite direction of the solution delivery member 708, and in this case get deposited onto the lead roller 701. Rollable devices 710 are shown disposed in the gap 704 between the rollers.

Figure 32:
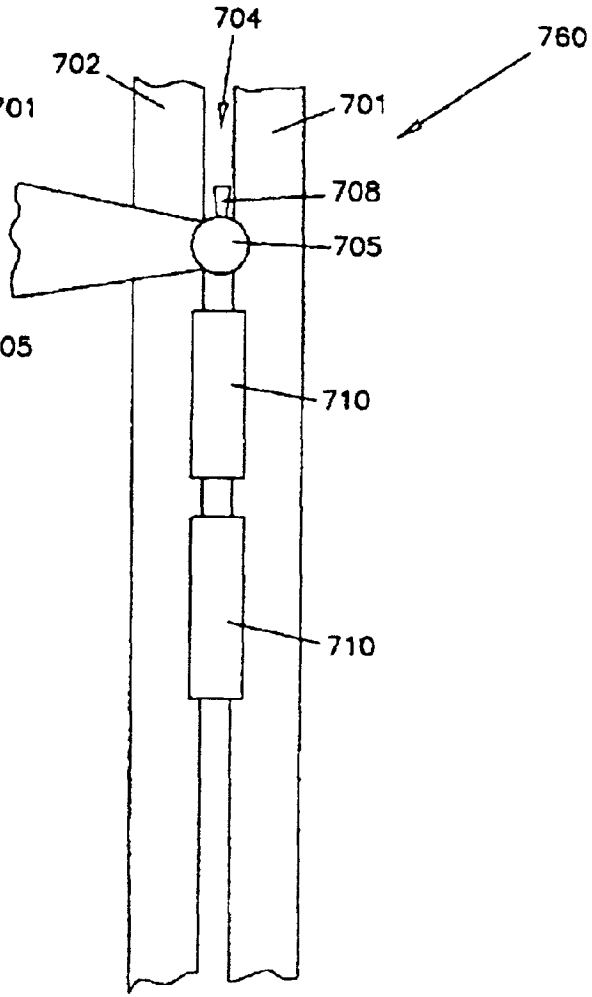
FIG. 32 is a schematic top view of a coating apparatus in accordance with an embodiment of the invention having a solution delivery member arranged in a third configuration.
Figure 31:
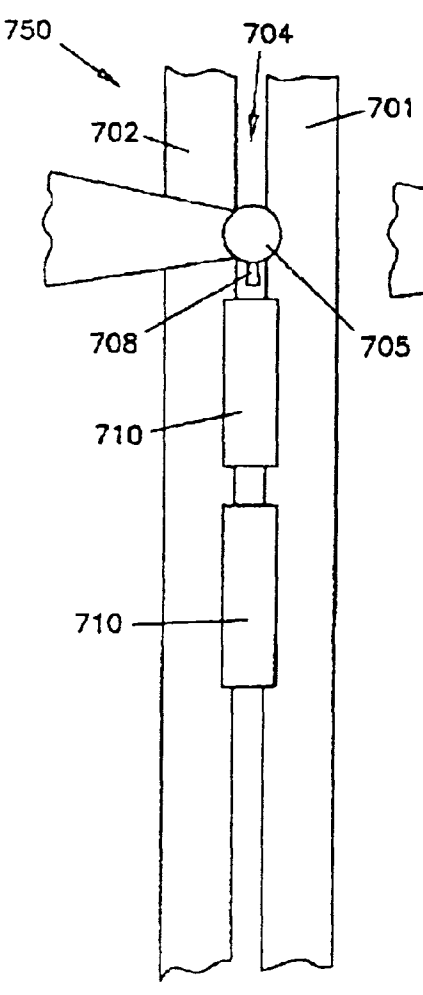
FIG. 31 is a schematic top view of a coating apparatus in accordance with an embodiment of the invention having a solution delivery member arranged in a second configuration.
Figure 33:
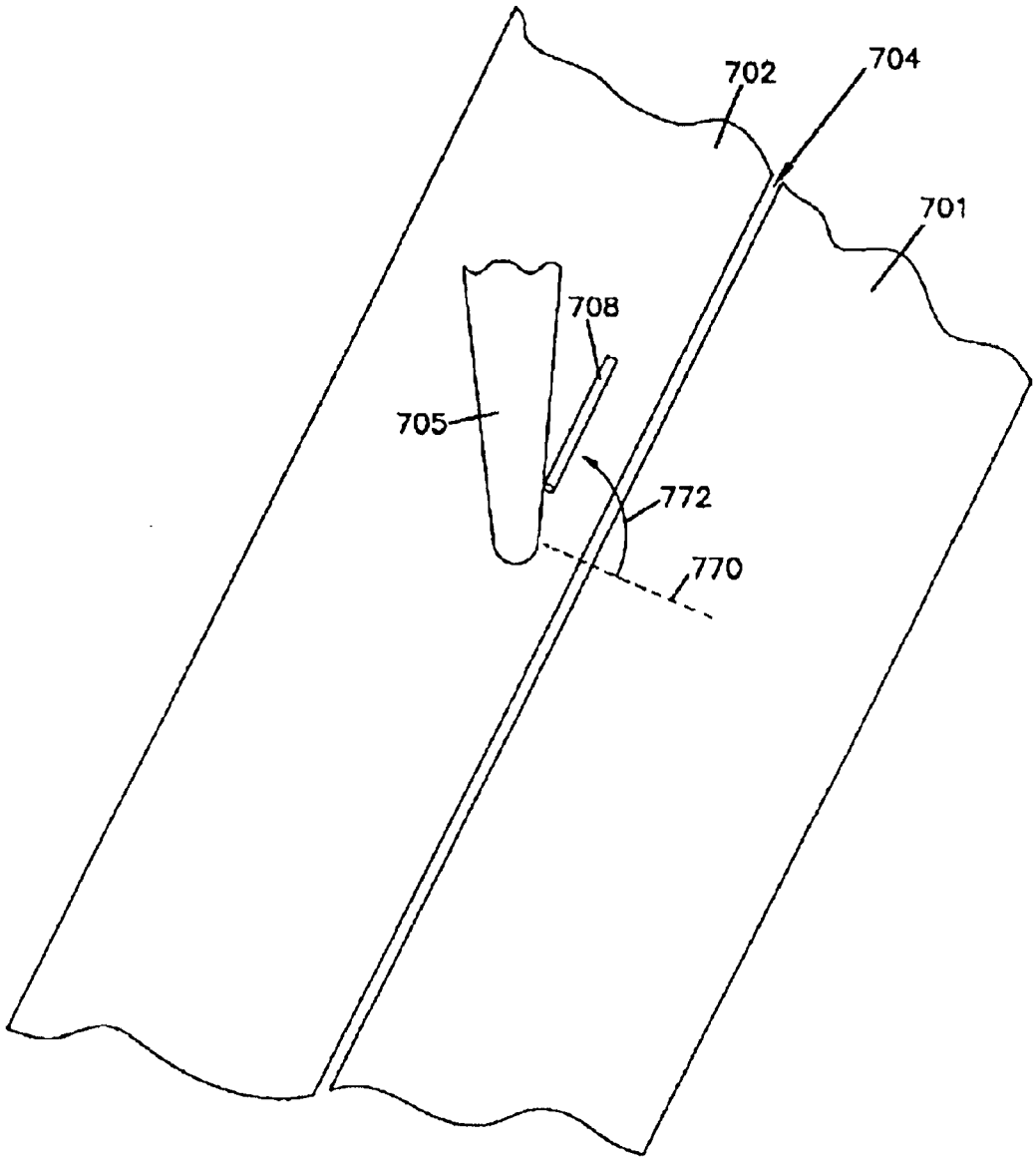
FIG. 33 is a perspective view of a coating head and a solution delivery member.

Referring now to FIGS. 31 and 32, the solution delivery member 708 can be repositioned so that it is in a plane that is generally parallel to the rollers 701, 702 and the gap 704. In this manner, the overspray 714 (as shown in FIG. 29) that was being deposited onto the lead roller 701 now passes through the gap 704 between rollers. FIG. 32 differs from FIG. 31 in that the solution delivery member 708 is positioned 180 degrees differently when view from the top angle. However, in both FIGS. 31 and 32, the solution delivery member 708 is disposed in a plane that is roughly parallel to the major axis of the rollers 701, 702, and the gap 704. Referring now to FIG. 33, a perspective view of a coating hand and a solution delivery member is shown. Solution delivery member 708 has been moved in the direction of arrow 772 from phantom line 770. In this manner, solution delivery member 708 is now roughly parallel to the gap 704 disposed between the pair of rollers 701, 702. One of skill in the art will appreciate that solution delivery member 708 could also be moved in the opposite direction of arrow 772 from phantom line 770 in order to be roughly parallel to the gap 704 disposed between the pair of rollers 701, 702.

Static Discharge

Static electricity is a non-moving electrical charge on an object. As stated above, it is believed that sticking and/or the movement of rollable devices out of the proper coating position is at least partly due to the rollable device carrying a static charge and the resulting electrostatic attraction and repulsion. In an embodiment, the invention includes a method including discharging a static charge on a device to be coated. In an embodiment, the invention includes an apparatus having a discharging member.

In some coating systems, the devices to be coated must be handled. For example, in some coating systems devices to be coated must be physically placed onto rollers of the coating system. As many devices to be coated may be implanted medical devices, they must be handled in accordance with "clean room" procedures. Frequently, such procedures involve the use of latex or nitrile gloves when physically handling the device to be coated. However, latex and nitrile materials generally act as insulators. Thus, contacting devices to be coated while wearing a latex or nitrile glove generally does not result in the static charge being dissipated.

In an embodiment, the devices to be coated are handled in a manner to release any static charge that they may hold. In an embodiment, conductive gloves are worn that allow the static charge on the device to be coated to be dissipated. By way of example, conductive gloves are available from QRP Gloves, Inc., Tucson, Ariz. In an embodiment, grounding wrist straps are worn by the personal handling the devices to be coated. In an embodiment, the devices are handled by individuals not wearing insulating gloves.

One of skill in the art will appreciate that a static charge can be discharged in a variety of ways. In some embodiments, discharge involves contacting the device to be coated with an object that is grounded or relatively grounded to reduce or eliminate the static charge. For example, the device to be coated may be contacted by a conductor that is grounded. In an embodiment, the conductor can be a part of the coating apparatus. In an embodiment, the conductor is separate from the coating apparatus.

In an embodiment, the invention includes an ionizer. An ionizer generates positive and negative ions, for example in a gaseous state, that can then be directed at the device to be coated. Those ions that are of the opposite charge to that which exists on the device to be coated will be attracted to the device to be coated and act to neutralize the static charge. In an embodiment, the invention includes an ionizing blower. By way of example, ionizing blowers such as the Critical Environment Ionizer Model 5810 are available from Ion Technology, Berkeley, Calif.

Masking Member

In an embodiment, the invention includes a masking member that is disposed over the device to be coated or disposed over the rollers. By way of example, the masking member can be used to further control the spray pattern produced by the spray nozzle. In an embodiment, the masking member can be used to prevent deposition of a spray solution onto certain portions of a device to be coated. By way of example, the masking member can cover the center of a device to be coated so that when a spray nozzle passes over the device, the spray pattern is deposited only upon the ends of the device. By way of further example, the masking member can be adapted and configured to cover the rollers but not the gap between the rollers. In an embodiment, the masking member can prevent spray solution from being deposited on the rollers.

Figure 34:
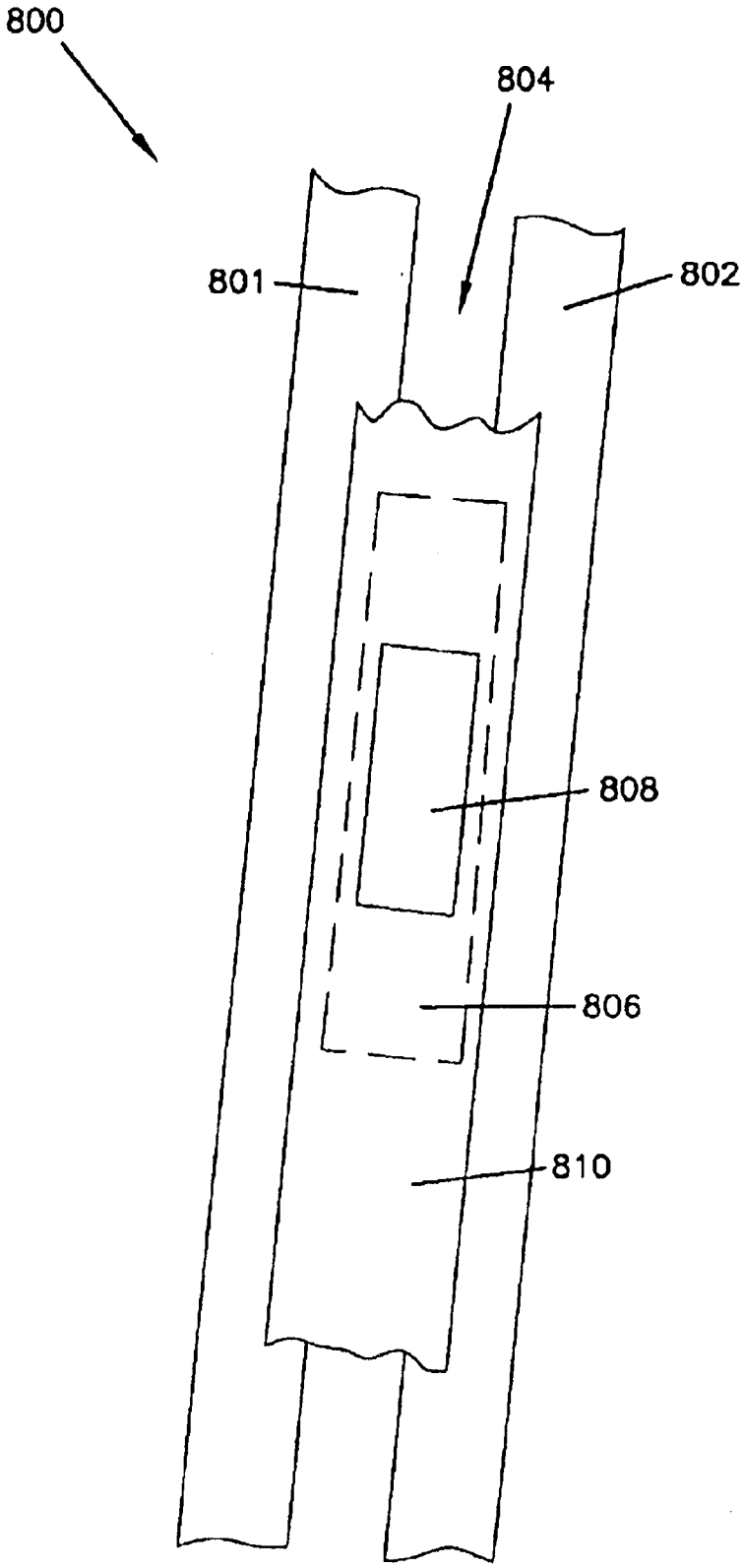
FIG. 34 is a top perspective view of a coating apparatus in accordance with an embodiment of the invention having a masking member.

Referring now to FIG. 34, a schematic top view is shown of an embodiment of the invention including a masking member. A first roller 801 and a second roller 802 are separated by a gap 804. A device to be coated 806, visible in phantom lines, is disposed in the gap 804 between the pair of rollers. A masking member 810 is disposed over the pair of rollers and the gap 804. The masking member 810 has an aperture 808 through which a spray pattern can proceed such that the spray is deposited only on those portions of the device 806 that are not covered by the masking member 810. In an embodiment, the masking member may include a plurality of apertures.

Coating Material

Any compound that can provide a homogenous coating material can be used. A wide range of compounds and solvents can be sprayed onto the device, including compounds and agents that may improve the function of the device, for example, the function of an implantable medical device in vivo. These improvements can be manifested for example, in increased biocompatibility or lubricity of the coated device. Such compounds or agents can include biologically active agents, such as pharmaceuticals, or other compounds such as polymers, for example, hydrophilic or hydrophobic polymers. Typically, these compounds or agents can be suspended or dissolved in a solvent and then deposited on the device via the spray nozzle. A wide variety of solvents can be used, ranging from polar to nonpolar solvents. Solvents can include alcohols (e.g., methanol, butanol, propanol, and isopropanol), alkanes (e.g., halogenated or unhalogenated alkanes such as hexane and cyclohexane), amides (e.g., dimethylformamide), esters (e.g., THF and dioxolane), ketones (e.g., methylethylketone), aromatic compounds (e.g., toluene and xylene), nitrites (e.g., acetonitrile) and esters (e.g., ethyl acetate). In an embodiment, the solvent is one in which a polymer component(s) forms a true solution. In an embodiment, the solvent is THF.

In an embodiment, the coating material includes an active agent in combination with at least one polymer. In an embodiment, the coating material includes an active agent in combination with a plurality of polymers, including a first polymer and a second polymer. When the coating material contains only one polymer, it can be either a first or second polymer as described herein. As used herein, term "(meth) acrylate" when used in describing polymers shall mean the form including the methyl group (methacrylate) or the form without the methyl group (acrylate).

Examples of suitable first polymers include poly(alkyl (meth)acrylates), and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with molecular weights ranging from about 200,000 daltons to about 320,000 daltons, and with varying inherent viscosity, solubility, and form (e.g., as crystals or powder).

Examples of suitable first polymers also include polymers selected from the group consisting of poly(aryl(meth) acrylates), poly(aralkyl(meth)acrylates), and poly (aryloxyalkyl (meth)acrylates). Such terms are used to describe polymeric structures wherein at least one carbon chain and at least one aromatic ring are combined with acrylic groups, typically esters, to provide a composition of this invention. In particular, preferred polymeric structures are those with aryl groups having from 6 to 16 carbon atoms and with weight average molecular weights from about 50 to about 900 kilodaltons. Suitable poly(aralkyl(meth) acrylates), poly(arylalky(meth)acrylates) or poly (aryloxyalkyl(meth)acrylates) can be made from aromatic esters derived from alcohols also containing aromatic moieties. Examples of poly(aryl(meth) acrylates) include poly (9-anthracenyl methacrylate), poly (chlorophenyl acrylate), poly(methacryloxy-2-hydroxybenzophenone), poly (methacryloxybenzotriazole), poly (naphthyl acrylate) and -methacrylate), poly(4-nitrophenyl acrylate), poly (pentachloro(bromo, fluoro)acrylate) and -methacrylate), and poly(phenyl acrylate) and -methacrylate). Examples of poly(aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl (meth)acrylates) include poly(phenoxyethyl acrylate) and -methacrylate), and poly (polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture for use in this invention includes mixtures of pBMA and pEVA. This mixture of polymers has proven useful with absolute polymer concentrations (i.e., the total combined concentrations of both polymers in the coating material), of between about 0.25 and about 70 percent (wt). It has furthermore proven effective with individual polymer concentrations in the coating solution of between about 0.05 and about 70 percent (wt). In one preferred embodiment the polymer mixture includes pBMA with a molecular weight of from 100 kilodaltons to 900 kilodaltons and a pEVA copolymer with a vinyl acetate content of from 24 to 36 weight percent. In a particularly preferred embodiment the polymer mixture includes pBMA with a molecular weight of from 200 kilodaltons to 400 kilodaltons and a pEVA copolymer with a vinyl acetate content of from 30 to 34 weight percent. The concentration of the active agent or agents dissolved or suspended in the coating mixture can range from 0.01 to 90 percent, by weight, based on the weight of the final coating material.

Second polymers of the invention can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. First polymers of the invention can also comprise a polymer selected from the group consisting of poly(alkyl(meth)acrylates) and poly (aromatic (meth)acrylates), where "(meth)" will be understood by those skilled in the art to include such molecules in either the acrylic and/or methacrylic form (corresponding to the acrylates and/or methacrylates, respectively).

Poly(alkylene-co-alkyl(meth)acrylates) include those copolymers in which the alkyl groups are either linear or branched, and substituted or unsubstituted with non-interfering groups or atoms. Such alkyl groups preferably comprise from 1 to 8 carbon atoms, inclusive, and more preferably, from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25 to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, second polymers for use in this invention can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly (ethylene-co-1-octene).

"Polybutenes" suitable for use in the present invention includes polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative second polymers include diolefin-derived, non-aromatic polymers and copolymers, including those in which the diolefin monomer used to prepare the polymer or copolymer is selected from butadiene ($CH_2{=}CH{-}CH{=}CH_2$) and/or isoprene ($CH_2{=}CH{-}C(CH_3){=}CH_2$). In an embodiment, the polymer is a homopolymer derived from diolefin monomers or is a copolymer of diolefin monomer with non-aromatic monoolefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl(meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a Mw between about 150 kilodaltons and about 1,000 kilodaltons. In an embodiment, polymers and copolymers have a Mw between about 200 kilodaltons and about 600 kilodaltons.

Additional alternative second polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$–$C_4$ alkyl(meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative second polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have an Mw from about 100 kilodaltons to about 300 kilodaltons.

Polymers can also include a poly(ether ester) multiblock copolymer based on poly(ethylene glycol) (PEG) and poly (butylene terephthalate) and can be described by the following general structure:

$$[—(OCH_2CH_2)_n—O—C(O)—C_6H_4—C(O)—]_x[—O—(CH_2)_4—O—C(O)—C_6H_4—C(O)—]_y,$$

where $—C_6H_4—$ designates the divalent aromatic ring residue from each esterified molecule or terephthalic acid, n represents the number of ethylene oxide units in each hydrophilic PEG block, x represents the number of hydrophilic blocks in the copolymer, and y represents the number of hydrophobic blocks in the copolymer. Preferably, n is selected such that the molecular weight of the PEG block is between about 300 and about 4000. Preferably, x and y are selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Degradation of the copolymer does not create toxic degradation products or an acid environment, and its hydrophilic nature conserves the stability of labile active agents, such as proteins (e.g., lysozymes). Microspheres containing mixtures of block copolymers and active agents can easily be designed for use in situations requiring faster degradation.

In an embodiment, polymer systems of the present invention include microspheres based on dextran microspheres cross-linked through ester linkages. The microspheres are produced using a solvent-free process, thus avoiding the possibility of denaturing incorporated protein molecules. Loading levels as high as 15% (wt) protein can be achieved along with high encapsulation efficiencies (typically greater than 90%). Microsphere sizes of less than 50 um are possible, allowing for subcutaneous injection. The microsphere particles degrade through bulk erosion rather than surface erosion. No acidification occurs upon degradation, thus preserving the structural integrity of the protein molecules.

Polymers of the invention also include biodegradable polymers. Suitable biodegradable polymeric materials are selected from: (a) non-peptide polyamino polymers; (b) polyiminocarbonates; (c) amino acid-derived polycarbonates and polyarylates; and (d) poly(alkylene oxide)polymers. The biodegradable polymeric materials can break down to form degradation products that are non-toxic and do not cause a significant adverse reaction from the body.

In an embodiment, the biodegradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, comprising two or three amino acid units having one of the following two structures illustrated below:

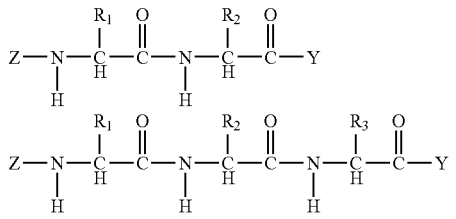

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are nontoxic, are biodegradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the biodegradable polymeric material can be composed of polyiminocarbonates. Polyiminocarbonates are structurally related to polycarbonates, wherein imino groups (>C═NH) are present in the places normally occupied by carbonyl oxygen in the polycarbonates. Thus, the biodegradable component can be formed of polyiminocarbonates having linkages

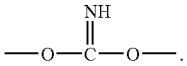

For example, one useful polyiminocarbonate has the general polymer structural formula

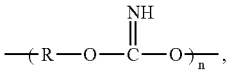

wherein R is an organic divalent group containing a non-fused aromatic organic ring, and n is greater than 1. Preferred embodiments of the R group within the general formula above is exemplified by, but is not limited to the following:

R group (a)

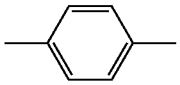

(b)

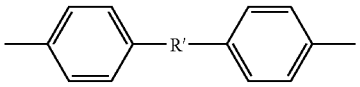

wherein R' is lower alkene $C_1$ to $C_6$ (c)

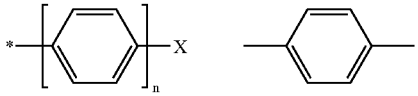

wherein n is an integer equal to or greater than 1, X is a hetero atom such as —O—, —S—, or a bridging group such as —NH—, —S(═O)—, —$SO_2$—, —C(═O)—, —$C(CH_3)_2$—, —$CH(CH_3)$—, —$CH(CH_3)$—$CH_2$—$CH(CH_3)$—, (d)

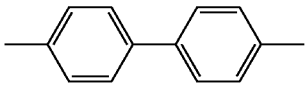

Also, compounds of the general formula

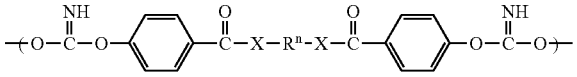

can be utilized, wherein X is O, NH, or NR'''', wherein R'''' is a lower alkyl radical; and R'' is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

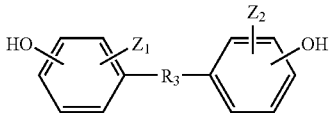

and dicyanate compounds having the formula

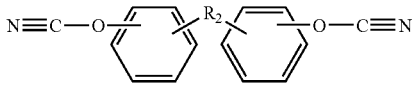

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Preferably, each of $Z_1$ and $Z_2$ are hydrogen.

In an embodiment, the biodegradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. Exemplary amino acid-derived diphenol starting materials for the preparation of the amino acid-derived polycarbonates and/or polyarylates of this embodiment are monomers that are capable of being polymerized to form polyiminocarbonates with glass transition temperatures ("Tg's") sufficiently low to permit thermal processing. The monomers according to this embodiment are diphenol compounds that are amino acid ester derivatives having the formula shown below:

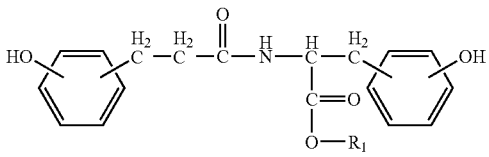

in which $R_1$ is an alkyl group containing up to 18 carbon atoms.

In yet another embodiment, the biodegradable polymeric material can be composed of copolymers containing both hydrophilic poly(alkylene oxides) (PAO) and biodegradable sequences, wherein the hydrocarbon portion of each PAO unit contains from 1 to 4 carbon atoms, or 2 carbon atoms (i.e., the PAO is poly(ethylene oxide)). For example, useful biodegradable polymeric materials can be made of block copolymers containing PAO and amino acids or peptide sequences and contain one or more recurring structural units independently represented by the structure —L—$R_1$—L—$R_2$—, wherein $R_1$ is a poly(alkylene oxide), L is —O— or —NH—, and $R_2$ is an amino acid or peptide sequence containing two carboxylic acid groups and at least one pendent amino group. Other useful biodegradable polymeric materials are composed of polyarylate or polycarbonate random block copolymers that include tyrosine-derived diphenol monomers and poly(alkylene oxide), such as the polycarbonate shown below:

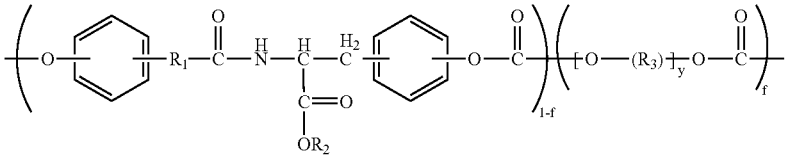

wherein $R_1$ is —CH═CH— or $(—CH_2—)_j$, in which j is 0 to 8; $R_2$ is selected from straight and branched alkyl and alkylaryl groups containing up to 18 carbon atoms and optionally containing at least one ether linkage, and derivatives of biologically and pharmaceutically active compounds covalently bonded to the copolymer; each $R_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

The coating material can also include natural polymers such as polysaccharides such as polydextrans, glycosaminoglycans such as hyaluronic acid, and polypeptides or soluble proteins such as albumin and avidin, and combinations thereof. Combinations of natural and synthetic polymers can also be used. The synthetic and natural polymers and copolymers as described can also be derivitized with a reactive group, for example, a thermally reactive group or a photoreactive group.

Photoactivatable aryl ketones are preferred, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The coating material can also contain one or more biologically active agents. An amount of biologically active agent can be applied to the device to provide a therapeutically effective amount of the agent to a patient receiving the coated device. Particularly useful agents include those that affect cardiovascular function or that can be used to treat cardiovascular-related disorders.

Active agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, anti-metabolites, miotic agents, anti-proliferatives, anticancer chemotherapeutic agents, anti-neoplastic agents, antipolymerases, antivirals, anti-AIDs substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, anti-oxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL®, paclitaxel, or the derivatives thereof, rapamycin, vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanaine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody, or another growth factor antagonist or agonist; dopamine, bromocriptine mesylate, pergolide mesylate, or another dopamine agonist; $^{60}$C (5.3 year half life), $^{192}$Ir (73.8 days), $^{32}$P (14.3 days), $^{111}$In (68 hours), $^{90}$Y (64 hours), $^{99}$Tc (6 hours), or another radio-therapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocophenol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating material include, but are not limited to, hormones, β-Blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftrizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatecho-1, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl L(−), deprenyl HCL D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, anti-sense molecules, androgenic receptor blockers and statin agents.

In an embodiment, the active agent can be in a microparticle. In an embodiment, microparticles can be dispersed on the surface of the substrate.

The weight of the coating attributable to the active agent can be in any range desired for a given active agent in a given application. In some embodiments, weight of the coating attributable to the active agent is in the range of about 1 microgram to about 10 milligrams of active agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In an embodiment, the weight of the coating attributable to the active agent is between about 0.01 mg and about 0.5 mg of active agent per $cm^2$ of the gross surface area of the device. In an embodiment, the weight of the coating attributable to the active agent is greater than about 0.01 mg.

In some embodiments, more than one active agent can be used as a part of the coating material. Specifically, co-agents or co-drugs can be used. A co-agent or co-drug can act differently than the first agent or drug. The co-agent or co-drug can have an elution profile that is different than the first agent or drug.

In some embodiments, the active agent can be hydrophilic. In an embodiment, the active agent can have a molecular weight of less than 5 kilodaltons and can have a water solubility of greater than 10 mg/mL at 25 degrees Celsius. In some embodiments, the active agent can be hydrophobic. In an embodiment, the active agent can have a water solubility of less than 10 mg/mL at 25 degrees Celsius.

It is understood that changes and modifications may be made thereto without departing from the scope and the spirit of the invention as hereinafter claimed. The invention will now be demonstrated referred to the following non-limiting examples.

EXAMPLES

Example 1

Coating Apparatus

An automated coating apparatus having an ultrasonic spray nozzle (Sono Tek; Milton, N.Y.) attached to a robotic arm was used to coat stainless steel stents. A coating solution was supplied to the spray nozzle using syringe pump (kdScientific Inc., New Hope, Pa.). Stents were placed in the groove on pairs of rollers, above the gap between the each roller of the pair. A total of six pairs of rollers were attached to a tray and brought into a coating zone. The spray nozzle travels over the each roller, dispensing coating solution in a narrow band on the stents. When the spray nozzle reaches the end of Roller #6, Rollers #1–3 index and rotate the stents. When the spray nozzle reaches the end of Rollers #3, Rollers #4–6 index. The capacity of the coating apparatus is about 50 stents, each stent 18 mm in length.

Example 2

Application of a Base Coat Material

The coating apparatus as described in Example 1 was used to provide a base coat to stents having a size of 18 mm in length by 1.5 mm in diameter. Based on the surface area of the stents, a basecoat weight range was chosen to be in the range of 600–660 μg per stent. Prior to the coating procedure, stents were individually weighed. Stents were placed on the pairs of rollers and a base coat material was deposited on the stents.

A coating solution was prepared containing pBMA (poly (butylmethacrylate)) at a concentration of 1.67 g/l, pEVA (poly(ethylene-co-vinyl acetate)) at a concentration of 1.67 g/l, and an immunosuppressive antibiotic at a concentration of 1.67 g/l, dissolved in tetrahydrofuran. The solution delivery rate from the nozzle was 0.15 ml/min; the nozzle air pressure was maintained at 2.5 psi; and the sonicator power was set at 0.6 watts. The distance from the nozzle tip to the surface of the stent was adjusted to be in the range of 2–3 mm and the nozzle travel speed along roller axis was 18 cm/sec.

The movement of the rollers during the indexing function was randomized and set at a 3.7:1 circumference to cycle pattern. Essentially, after a stripe of coating material was sprayed on a portion of the stent, the stent was randomly indexed to position another portion of the stent in line for an application of another stripe of coating material. Approximately 15 seconds lapsed between applications of the coating solution. The approximate width of the applied coating per stripe was 1 mm wide. 135 cycles of indexing and coating were performed on the stents. The stents were then dried under ambient conditions for at least 30 minutes after application of the final coating.

Figure 35:
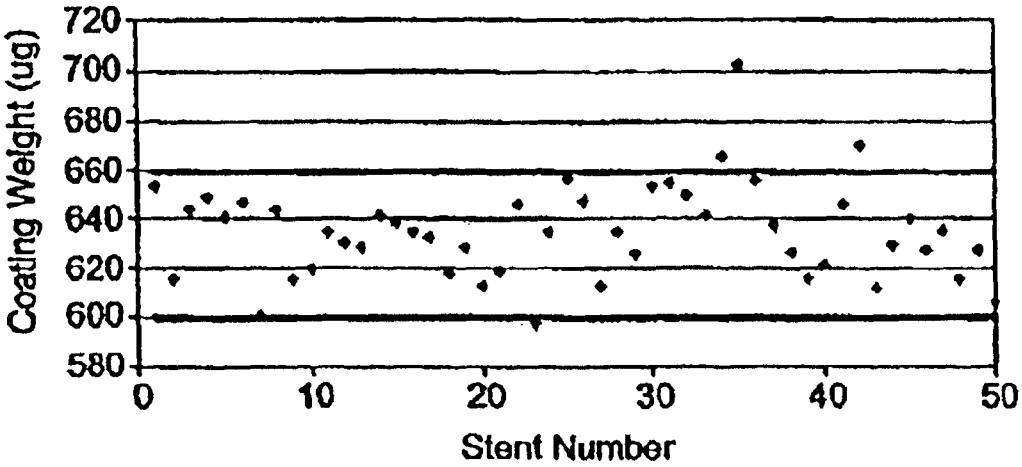
FIG. 35 is a graph illustrating the weight of applied coating material (Y axis) and the stent member (X axis) obtained from a coating procedure using the current invention.

After the coating on the stents had dried each coated stent was weighed to determine the amount of base coating applied. FIG. 35 illustrates the results of the coating process. FIG. 35 indicates that the average basecoat weight applied was 635 μg±19 μg and that 92.0% of the stents fell within the target range of 600–660 μg of coating material applied per stent.

Figure 36:
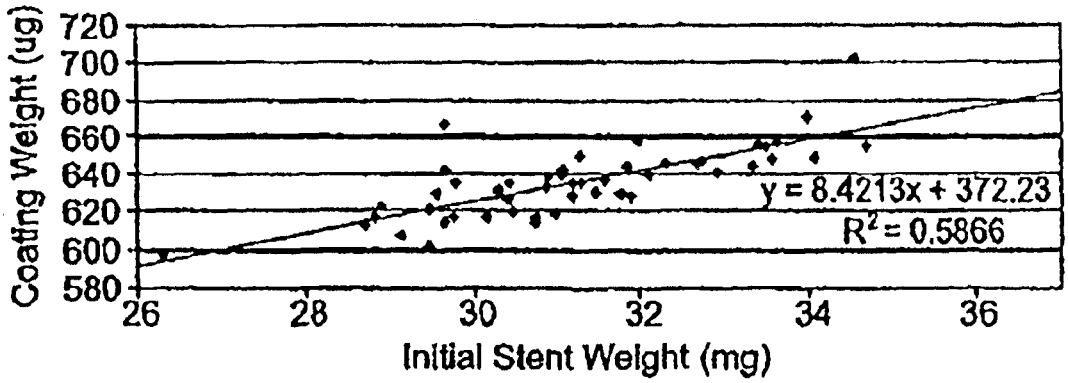
FIG. 36 is a graph illustrating the weight of applied coating material (Y axis) versus the initial stent weight (X axis) obtained from a coating procedure using the coating apparatus.

Since the starting weight varies from stent to stent, the accuracy in the amount of applied coating was also determined for each stent based on its starting weight. FIG. 36 illustrates the results and shows that variations in the amount of applied coating, as illustrated in FIG. 35, are primarily due to the variations in the starting weight of the stent and not variations in the coating process. FIG. 36 shows that as the initial stent weight increased (which correlates to an increase in coatable surface area on the stent), the amount of coating material applied to each stent increased. According to this graph, points along the line represent the target coating weights based on the initial starting weight of the stent. The data shows that, on average, the actual weight of the applied coating did not deviate more than 0.31% from the target weight based on the starting weight of individual stents.

Figure 37:
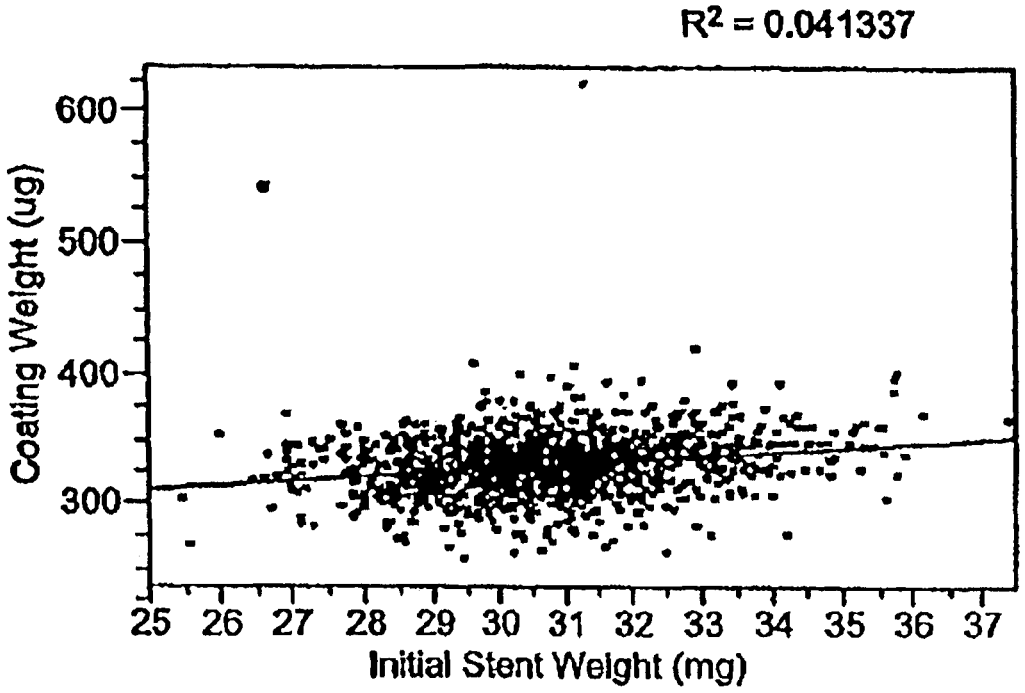
FIG. 37 is a graph showing a comparative example with the weight of applied coating material (Y axis) versus the initial stent weight (X axis) obtained from a coating procedure using a traditional coating apparatus.

The improvement in coating accuracy was assessed by comparing the results from the coating apparatus of the current invention, as detailed in FIG. 36, with coating results obtained from a traditional manual coater. FIG. 37 illustrates the initial stent weight and the amount of coating applied to each stent according to its initial weight. The data shows that using a traditional manual coater the actual weight of the applied coating, on average, deviated approximately 1.55% from the target weight based on the starting weight of individual stents.

This data represents that use of the coating apparatus of the current invention results in an improvement in coating accuracy of approximately 5 times as compared to traditional coating apparatus.

Other production lots of 18 mm by 1.5 mm stents were coated with a base coat material using the parameters described above. 86.5–95.4% of stents from these production lots were fell within the target range of 600–660 μg of coating material applied per stent with the average basecoat weight being 628–630 μg having a standard deviations ranging from 20–29 μg. This data indicates that the coating accuracy of the current invention is reproducible using various coatable devices.

The coated stents were microscopically examined and were found to have a consistently better appearance than traditionally coated stents.

The work time for the above-described coating procedure for 50 stents was calculated and compared to traditional manual coating methods. The time required to complete this coating process was reduced by approximately 80% relative to the traditional manual coating methods.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "of" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration to. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

I claim:

1. A method for coating a stent comprising the steps of:

a) placing the stent on a device rotator, the device rotator comprising a pair of rollers, the pair comprising a first roller and a second roller separated by a gap not wider than the device;

b) disposing a coating material on the stent, comprising spraying a coating material from a nozzle, wherein the nozzle is arranged to direct spray at the gap;

c) rotating the stent a first amount of rotation by rotating at least one of the first or second rollers in a first direction, the first amount of rotation sufficient to release sticking between the stent and the first or second roller; and d) rotating the stent a second amount of rotation by rotating at least one of the first or second rollers in a second direction, the first direction being opposite of the second direction; wherein the second amount of rotation is greater than the first amount of rotation.

2. The method of claim 1, further comprising repeating steps b) through d) a plurality of times.

3. The method of claim 1, further comprising moving the nozzle in a direction parallel to the first roller.

4. The method of claim 3, wherein the steps of disposing and moving are performed simultaneously.

5. The method of claim 1, wherein step c) is performed prior to the coating material being dry.

6. The method of claim 1, the nozzle comprising a sonicating member.

7. The method of claim 6, the sonicating member comprising a channel for gas flow.

8. The method of claim 1, the coating material comprising a material selected from the group consisting of poly (ethylene-co-vinyl acetate) and poly(n-butyl methacrylate).

9. The method of claim 1, the coating material comprising an active agent.

10. The method of claim 1, further comprising regulating the humidity, temperature, or both, around the stent.

11. The method of claim 1, the stent having a cylindrical shape and no greater than 2.0 mm in diameter.

12. The method of claim 1, wherein the steps are performed as part of a batch process for coating a plurality of medical devices.

* * * * *